(12) United States Patent
Akita et al.

(10) Patent No.: US 10,927,354 B2
(45) Date of Patent: Feb. 23, 2021

(54) D-TYPE AMINO ACID DEHYDROGENASE

(71) Applicants: Kureha Corporation, Tokyo (JP); National Institute Of Advanced Industrial Science And Technology, Tokyo (JP)

(72) Inventors: Hironaga Akita, Higashi-hiroshima (JP); Yuusuke Nakamichi, Higashi-hiroshima (JP); Masahiro Watanabe, Higashi-hiroshima (JP); Akinori Matsushika, Higashi-hiroshima (JP); Tomotake Morita, Tsukuba (JP)

(73) Assignees: KUREHA CORPORATION, Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/637,419

(22) PCT Filed: Aug. 9, 2018

(86) PCT No.: PCT/JP2018/029892
§ 371 (c)(1),
(2) Date: Feb. 7, 2020

(87) PCT Pub. No.: WO2019/031575
PCT Pub. Date: Feb. 14, 2019

(65) Prior Publication Data
US 2020/0224178 A1 Jul. 16, 2020

(30) Foreign Application Priority Data
Aug. 9, 2017 (JP) .............................. JP2017-154768

(51) Int. Cl.
| | |
|---|---|
| C12N 9/06 | (2006.01) |
| C12N 15/52 | (2006.01) |
| C12N 1/21 | (2006.01) |
| C12P 13/04 | (2006.01) |

(52) U.S. Cl.
CPC ............ *C12N 9/0014* (2013.01); *C12P 13/04* (2013.01); *C12Y 104/99001* (2013.01)

(58) Field of Classification Search
None
See application file for complete search history.

(56) References Cited

U.S. PATENT DOCUMENTS

2008/0182972 A1   7/2008   Rozzell

FOREIGN PATENT DOCUMENTS

JP        2017-108740 A       6/2017

OTHER PUBLICATIONS

Uni Prot Database Accession No. A0A1U9K4X8, Jul. 2017, 2 pages (Year: 2017).*
GenPept Accession No. WP_054948699, Oct. 2015, 1 page (Year: 2015).*
GenBank Database [online], Accession No. CP019699.1, dated Feb. 21, 2017, retrieved from Internet URL<https://www.ncbi.nlm.nih.gov/nuccore/1148968360>, pp. 1-864.
Akita, H. et al., "Thermostable artificial NADP+-dependent D-amino acid dehydrogenase: its creation and application," Vitamins (Japan) 2016, vol. 90 (11), pp. 544-554.
Akita, H. et al., "Creation of a thermostable NADP+-dependent D-amino acid dehydrogenase from Ureibacillus thermosphaericus strain A1 meso-diaminopimelate dehydrogenase by site-directed mutagenesis," Biotechnol Lett., published online May 22, 2012, vol. 34, pp. 1693-1699.
International Search Report of the International Searching Authority for PCT/JP2018/029892 dated Oct. 23, 2018.
English translation of International Search Report of the International Searching Authority for PCT/JP2018/029892 dated Oct. 23, 2018.
Written Opinion of the International Preliminary Examining Authority of PCT/JP2018/029892 dated Oct. 23, 2018.
English translation of Written Opinion of the International Preliminary Examining Authority of PCT/JP2018/029892 dated Oct. 23, 2018.
Notification of Reasons for Refusal First Office Action issued by the Japanese Patent Office for Japanese Patent Application 2019-535715 dated Jan. 21, 2020.
Translation of the Notification of Reasons for Refusal First Office Action issued by the Japanese Patent Office for Japanese Patent Application 2019-535715 dated Jan. 21, 2020.
First Office Action from CN Application No. 201880050600.5, dated Aug. 10, 2020, 9 pages.
Diaminopimelate Dehydrogenase [Numidum Massiliense], NCBI Reference Sequence: WP_054948699.1, Genbank, p. 1, Oct. 20, 2015, 2 pages.
Extended European Search Report from EP Application No. 18844470.7, dated May 26, 2020, 8 pages.
Database UniProtKB, A0A1U9K4X8_9BACL, Jun. 7, 2017, 6 pages.
Xiuzhen, Gao, et al., "A Newly Determined Member of the meso-Diaminopimelate Dehydrogenase Family with a Broad Substrate Spectrum", Applied and Environmental Microbiology, vol. 83, Issue 11, May 17, 2017, 10 pages.
Akita, Hironaga, et al., "Structural insight into the thermostable NADP+-dependent meso-diaminopimelate. dehydrogenase from Ureibacillus thermosphaericus", Biological Chrystallography, Accepted Feb. 22, 2015, vol. 71, No. 5, pp. 1136-1146.

(Continued)

*Primary Examiner* — David Steadman
(74) *Attorney, Agent, or Firm* — Abel Schillinger, LLP

(57) ABSTRACT

An enzyme has an activity of reversible dehydrogenation of D-amino acid and is a hexamer of polypeptides having an amino acid sequence that has 80% or more identity with the amino acid sequence of SEQ ID NO: 2. The amino acid sequence of the polypeptide can include one or more amino acid substitutions for one or more amino acid residues of SEQ ID NO: 2.

12 Claims, 6 Drawing Sheets

Specification includes a Sequence Listing.

(56) References Cited

OTHER PUBLICATIONS

Lagier, Jean-Christophe, et al., "Non-contiguous finished genome sequence and description of *Herbaspirillum massiliense* sp. nov.", Standards in Genomic Sciences, The Genomic Standards Consortium, vol. 7, No. 2, Dec. 15, 2012, pp. 200-209.

Hironaga, Akita, et al., "Artificial Thermostable D-Amino Acid Dehydrogenase: Creation and Application", Frontiers in Microbiology, vol. 9, Aug. 3, 2018, 11 pages.

Cho, Yong-Joon, et al., "The Genome Sequence of '*Mycobacterium massiliense*' Strain CIP 108297 Suggests the Independent Taxonomic Status of the *Mycobacterium abscessus* Complex at the Subspecies Level", PLoS One, vol. 8, No. 11, Nov. 27, 2013, 19 pages.

* cited by examiner

CATATGAGTAATGTATACAACGTCGCCGTCGTCGGCTATGGTAATATCGGCAAGTACGCCGTGCAAGCAATCG
ATGCTGCTCCGGACATGCAATTAGCCGGTGTCGTCAGACGCGCGAGCTCCGCCGCGAAAGATACGCCGCCAGA
ACTCGTCGGACGCCGTGTCGTCCACGACATCCGCGACTTGGAGCAAGTCGACGTCGCCATCTTAGCGGCACCG
ACGCGGACGATTCGGGCGTACGCCCGGGACGTTCTCTCCCTGGGCATTCACACGGTCGACAGTTACGACATTC
ACGGCGAACTCGCTAACTTGCGGCGCGAGTTAGACGATGTGTCTAAAAAAAACGACAGCGTCGCCATCATTTC
CGCAGGCTGGGATCCGGGAACCGACTCGATGATTCGCGGCATGCTCGAGTTTATGGCGCCAGGTGGGTTAACG
TATACGAATTTTGGGCCCGGTATCGAGTATGGGGCACTCCGTCGCCGTCAAAGCGATCGACGGGTCAAAGACG
CGCTGTCCTTGACAATCCCCGCTCGGTACGAGCATCCACCGGCGCATGGTGTACGTCGAACTAGAAGCAGGTGC
CGATTCCAAACGGTCAAAAAGGCAATTTTAGCAGATCCGTATTTCGTCAACGACGAGACTCATGTGACGCAA
GTTCCTAACGTACAGCAACTCGTCAACGTCGGTCACGGAGTCTCCATGGAACGGAGAGGCGTATCCGGGGCGA
CGCACAACCAACTGTTCACGTTCGAGATGCGCATTAACAACCCGGCACTGACGTCGCAAGTGCTCGTCGCCGC
TGCCCGCGCGACGTTCAAACAGCAACCGGGTGCGTACACGATGATCGAGGTACCGGTAATCGATTATCTCCCT
GGCGACCGGGACGACATTATTCGGCGGTTAGTGTAAGAATTC
(SEQ ID NO: 1)

FIG. 1

MSNVTNVAVVGYCNIGKIAVQAIRAAPDMQLAGVVRRASSAAKDTPPELVGRRVVHDIRDLEGVDVAILAAPI
RTIPAYARDVLSLGIRTVDSYDIHGELANLRRELDDVSKKSDSVAIISAGVDPGTDSMIRGMLEFMAPGGLIY
TNFGPGMSMGHSVAVRAIDGVKDALSLTIPLGISIHREMVYVELEAGADFETVRKAILADPYFVNDETHVTQV
PNVQQLVNYGHGVSMERRGVSGATDNQLPTFEMRINNPALTSQVLVAAARATFKQQPGAVTMIEVPVIDYLPG
DRDDIIRRLY
(SEQ ID NO: 2)

FIG. 2

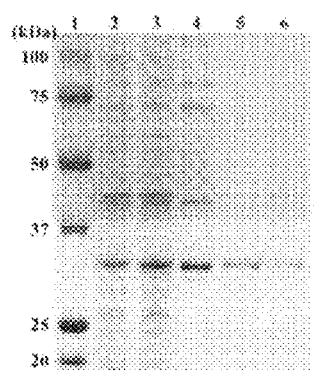

FIG. 3

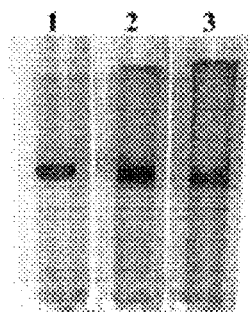

FIG. 4

CATATGAGTAATGTATACAACGTCGCCGTCGTCGGCTATGGTAATATCGGCAAGTACGCCGTGCAAGC
AATCGATGCTGCTCCGGACATGCAATTAGCCGGTGTCGTCAGACGCGCGAGCTCCGCCGCGAAAGATA
CGCCGCCAGAACTCGTCGGACGCCGTGTCGTCCACGACATCCGCGACTTGGAGCAAGTCGACGTCGCC
ATCTTAGCGGCACCGACGCGGACGATTCCGGCGTACGCCCGGACGTTCTCTCCCTCGGCATTCACAC
GGTCGACAGTTACGACATTCACGGCGAACTCGCTAACTTGCGGCGCGAGTTAGACGATGTGTCTAAAA
AAAACGACAGCGTCGCCATCATTTCCGCAGGCTGGGATCCGGGAACCGACTCGATGATTCGCGGCATG
CTCGAGTTTATGGCGCCAGGTGGGTTAACGTATACGAATTTTGGGCCCGGTATGAGTATGGGGCACTC
CGTCGCCGTCAAAGCGATCGACGGGGTCAAAGACGCGCTGTCCTTGATTATCCCGCTCGGTACGAGCA
TCCACCGGATGATGGTGTACGTCGAACTAGAAGCAGGTGCCGATTTCGAAACGGTCAAAAAGGCAATT
TTAGCAGATCCGTATTTCGTCAACGACGAGACTCATGTGACGCAAGTTCCTAACGTACAGCAACTCGT
CAACGTCGGTAACGGAGTCTCCATGGAACGGAGAGGCGTATCCGGGGCGACGCACAACCAACTGTTCA
CGTTCGAGATGCGCATTAACAACCCGGCACTGACGTCGCAAGTGCTCGTCGCCGCTGCCCGCGCGACG
TTCAAACAGCAACCGGGTGCGTACACGATGATCGAGGTACCGGTAATCGATTATCTCCCTGCCGACCG
GGACGACATTATTCGGCGGTTAGTGTAAGAATTC
(SEQ ID NO: 7)

FIG. 12

MSNVYNVAVVGYGNIGKYAVQAIDAAPDMQLAGVVRRASSAAKDTPPELYGRRVVHDIRDLEQVDVAI
LAAPTRTIPAYARDVLSLGIHTVDSYDIHGELANLRRELDDVSKKNDSVAIISAGWDPGTDSMIRGML
EFMAPGGLTYTNFGPGMSMGHSVAVKAIDGVKDALSLIIPLGTSIHRMMYYVELEAGADFETVKKAIL
ADPYFVNDETHVTQVPNVQQLVNVGNGVSMERRGVSGATHNQLFTFEMRINNPALTSQVLVAAARATF
KQQPGAYTMIEVPVIDYLPGDRDDIIRRLV
(SEQ ID NO: 8)

FIG. 13

CATATGAGTAATGTATACAACGTCGCCGTCGTCGGCTATGGTAATATCGGCAAGTACGCCGTGCAAGC
AATCGATGCTGCTCCGGACATGCAATTAGCCGGTGTCGTCAGACGCGCGAGCTCCGCCGCGAAAGATA
CGCCGCCAGAACTCGTCGGACGCCGTGTCGTCCACGACATCCGCGACTTGGAGCAAGTCGACGTCGCC
ATCTTAGCGGCACCGACGCGGACGATTCCGGCGTACGCCCGGACGTTCTCTCCCTCGGCATTCACAC
GGTCGACAGTTACTCCATTCACGGCGAACTCGCTAACTTGCGGCGCGAGTTAGACGATGTGTCTAAAA
AAAACGACAGCGTCGCCATCATTTCCGCAGGCTGGGATCCGGGAACCGACTCGATGATTCGCGGCATG
CTCGAGTTTATGGCGCCAGGTGGGTTAACGTATACGAATTTTGGGCCCGGTATGAGTTTAGGGCACTC
CGGTGCCGTCAAAGCGATCGACGGGGTCAAAGACGCGCTGTCCTTGATTATCCCGCTCGGTACGAGCA
TCCACCGGATGATGGTGTACGTCGAACTAGAAGCAGGTGCCGATTTCGAAACGGTCAAAAAGGCAATT
TTAGCAGATCCGTATTTCGTCAACGACGAGACTCATGTGACGCAAGTTCCTAACGTACAGCAACTCGT
CAACGTCGGTAACGGAGTCTCCATGGAACGGAGAGGCGTATCCGGGGCGACGCACAACCAACTGTTCA
CGTTCGAGATGCGCATTAACAACCCGGCACTGACGTCGCAAGTGCTCGTCGCCGCTGCCCGCGCGACG
TTCAAACAGCAACCGGGTGCGTACACGATGATCGAGGTACCGGTAATCGATTATCTCCCTGCCGACCG
GGACGACATTATTCGGCGGTTAGTGTAAGAATTC
(SEQ ID NO: 9)

FIG. 14

MSNVYNVAVVGYGNIGKYAVQAIDAAPDMQLAGVVRRASSAAKDTPPELVGRRVVHDIRDLEQVDVAI
LAAPTRTIPAYARDVLSLGIHIVDSYSIHGELANLRRELDDVSKKNDSVAIISAGWDPGTDSMIRGML
EFMAPCGLTYTNFGPGMSLGHSGAVKAIDGVKDALSLIPLGTSIHRMVYVELEAGADFETVKKAIL
ADPYFVNDETHVTQVPNVQQLVNVGNVSMERRGYSGATHNQLFTFEMRINNPALTSQVLVAAARATP
KQQPGAYTMIEVPVIDYLPGDRDDIIRRLV (SEQ ID: 10)

FIG. 15

CATATGAGTAATGTATACAACGTCGCCGTCGTCGGCTATGGTAATATCGGCAAGTACGCCGTGCAAGC
AATCGATGCTGCTCCGGACATGCAATTAGCCGGTGTCGTCAGACGCGCGAGCTCCGCCGCGAAAGATA
CGCCGCCAGAACTCGTCGGACGCCGTCGTCCACGACATCCGCGACTTGGAGCAAGTCGACGTCGCC
ATCTTAGCGGCACCGACGCGACGATTCCGGCGTACGCCCGGGACGTTCTCTCCCTCGGCATTCACAC
GGTCGACAGTTACGACATTCACGGCGAACTCGCTAACTTGCGGCGCGAGTTAGACGATGTGTCTAAAA
AAAACGACAGCGTCGCCATCATTTCCGCAGGCTGGGATCCGGGAACCGACTGATGATTCGCGGCATG
CTCGAGTTTATGGCGCCAGCTGGGTTAACGTATACGAATTTTGGCCCGGTATGAGTTTAGGGCACTC
CGGTCCCGTCAAAGCGATCGACGGGTCAAAGACGCGCTGTCCTTGATTATCCCGCTCGGTACGAGCA
TCCACCGGATGATGGTGTACGTCGAACTAGAAGCAGGTGCCGATTTCGAAACGGTCAAAAAGGCAATT
TTAGCAGATCCGTATTTCGTCAACGACGAGACTCATGTGACGCAAGTTCCTAACGTACAGCAACTCGT
CAACGTCGGTAACGAGTCTCCATGGAACGGAGAGGCGTATCCGGGCGACGCACAACCAACTGTTCA
CGTTCGAGATGCGCATTAACAACCGGCACTGACGTCGCAAGTGCTCGTCGCCGCTGCCCGGCGCACG
TTCAAACAGCAACCGGGTGCGTACACGATGATCGAGGTACCGGTAATCGATTATCTCCCTGGCGACCG
GGACGACATTATTCGGCGCTTAGTGTAAGAATTC (SEQ ID: 13)

FIG. 16

MSNVYNVAVVGYGNIGKYAVQAIDAAPDMQLAGVVRRASSAAKDTPPELVGREVVHDIRDLEQVDVAI
LAAPTRTIPAYARDVLSLGIHIVDSYDIHGELANLRRELDDVSKKNDSVAIISACWDPGTDSMIRGML
EFMAPCGLTYTNFGPGMSLGHSGAVKAIDGVKDALSLIPLGTSIHRMVYVELEAGADFETVKKAIL
ADPYFVNDETHVTQVPNVQQLVNVGNVSMERRGYSGATHNQLFTFEMRINNPALTSQVLVAAARATP
KQQPGAYTMIEVPVIDYLPGDRDDIIRRLV (SEQ ID: 14)

FIG. 17

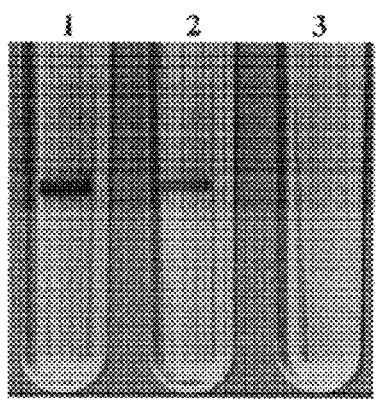

FIG. 18

```
                        SEQUENCE LISTING

<160> NUMBER OF SEQ ID NOS: 14

<210> SEQ ID NO 1
<211> LENGTH: 918
<212> TYPE: DNA
<213> ORGANISM: Numidum massiliense

<400> SEQUENCE: 1
catatgagta atgtatacaa cgtcgccgtc gtcggctatg gtaatatcgg caagtacgcc      60
gtgcaagcaa tcgatgctgc tccggacatg caattagccg gtgtcgtcag acgcgcgagc     120
tccgccgcga aagatacgcc gccagaactc gtcggacgcc gtgtcgtcca cgacatccgc     180
gacttggagc aagtcgacgt cgccatctta gcggcaccga cgcggacgat tccggcgtac     240
gcccgggacg ttctctccct cggcattcac acggtcgaca gttacgacat tcacggcgaa     300
ctcgctaact tgcggcgcga gttagacgat gtgtctaaaa aaaacgacag cgtcgccatc     360
atttccgcag gctgggatcc gggaaccgac tcgatgattc gcggcatgct cgagtttatg     420
gcgccaggtg ggttaacgta tacgaatttt gggcccggta tgagtatggg gcactccgtc     480
gccgtcaaag cgatcgacgg ggtcaaagac gcgctgtcct tgacaatccc gctcggtacg     540
agcatccacc ggcgcatggt gtacgtcgaa ctagaagcag gtgccgattt cgaaacggtc     600
aaaaaggcaa ttttagcaga tccgtatttc gtcaacgacg agactcatgt gacgcaagtt     660
cctaacgtac agcaactcgt caacgtcggt cacggagtct ccatggaacg gagaggcgta     720
tccggggcga cgcacaacca actgttcacg ttcgagatgc gcattaacaa cccggcactg     780
acgtcgcaag tgctcgtcgc cgctgcccgc ggacgttca aacagcaacc gggtgcgtac     840
acgatgatcg aggtaccggt aatcgattat ctccctggcg accgggacga cattattcgg     900
cggttagtgt aagaattc                                                   918

<210> SEQ ID NO 2
<211> LENGTH: 302
<212> TYPE: PRT
<213> ORGANISM: Numidum massiliense

<400> SEQUENCE: 2
```

Met Ser Asn Val Tyr Asn Val Ala Val Gly Tyr Gly Asn Ile Gly
1               5                   10                  15

Lys Tyr Ala Val Gln Ala Ile Asp Ala Ala Pro Asp Met Gln Leu Ala
            20                  25                  30

Gly Val Val Arg Arg Ala Ser Ser Ala Ala Lys Asp Thr Pro Pro Glu
                35                  40                  45

Leu Val Gly Arg Arg Val Val His Asp Ile Arg Asp Leu Glu Gln Val
    50                  55                  60

Asp Val Ala Ile Leu Ala Ala Pro Thr Arg Thr Ile Pro Ala Tyr Ala
65                  70                  75                  80

Arg Asp Val Leu Ser Leu Gly Ile His Thr Val Asp Ser Tyr Asp Ile
                85                  90                  95

His Gly Glu Leu Ala Asn Leu Arg Arg Glu Leu Asp Asp Val Ser Lys
            100                 105                 110

Lys Asn Asp Ser Val Ala Ile Ile Ser Ala Gly Trp Asp Pro Gly Thr
        115                 120                 125

Asp Ser Met Ile Arg Gly Met Leu Glu Phe Met Ala Pro Gly Gly Leu
    130                 135                 140

Thr Tyr Thr Asn Phe Gly Pro Gly Met Ser Met Gly His Ser Val Ala
145                 150                 155                 160

Val Lys Ala Ile Asp Gly Val Lys Asp Ala Leu Ser Leu Thr Ile Pro
                165                 170                 175

Leu Gly Thr Ser Ile His Arg Arg Met Val Tyr Val Glu Leu Glu Ala
            180                 185                 190

Gly Ala Asp Phe Glu Thr Val Lys Lys Ala Ile Leu Ala Asp Pro Tyr
        195                 200                 205

Phe Val Asn Asp Glu Thr His Val Thr Gln Val Pro Asn Val Gln Gln
    210                 215                 220

Leu Val Asn Val Gly His Gly Val Ser Met Glu Arg Arg Gly Val Ser
225                 230                 235                 240

Gly Ala Thr His Asn Gln Leu Phe Thr Phe Glu Met Arg Ile Asn Asn
                245                 250                 255

Pro Ala Leu Thr Ser Gln Val Leu Val Ala Ala Ala Arg Ala Thr Phe
            260                 265                 270

Lys Gln Gln Pro Gly Ala Tyr Thr Met Ile Glu Val Pro Val Ile Asp
        275                 280                 285

Tyr Leu Pro Gly Asp Arg Asp Asp Ile Ile Arg Arg Leu Val
    290                 295                 300

<210> SEQ ID NO 3
<211> LENGTH: 326
<212> TYPE: PRT
<213> ORGANISM: Bacillus sphaericus

<400> SEQUENCE: 3

Met Ser Ala Ile Arg Val Gly Ile Val Gly Tyr Gly Asn Leu Gly Arg
1               5                   10                  15

Gly Val Glu Phe Ala Ile Ser Gln Asn Pro Asp Met Glu Leu Val Ala
            20                  25                  30

Val Phe Thr Arg Arg Asp Pro Ser Th

```
            65                  70                  75                  80
Pro His Phe Ala Gln Trp Phe Asn Thr Ile Asp Ser Phe Asp Thr His
                    85                  90                  95

Ala Lys Ile Pro Glu Phe Phe Asp Ala Val Asp Ala Ala Gln Lys
                100                 105                 110

Ser Gly Lys Val Ser Val Ile Ser Val Gly Trp Asp Pro Gly Leu Phe
                115                 120                 125

Ser Leu Asn Arg Val Leu Gly Glu Ala Val Leu Pro Val Gly Thr Thr
            130                 135                 140

Tyr Thr Phe Trp Gly Asp Gly Leu Ser Gln Gly His Ser Asp Ala Val
145                 150                 155                 160

Arg Arg Ile Glu Gly Val Lys Asn Ala Val Gln Tyr Thr Leu Pro Ile
                    165                 170                 175

Lys Asp Ala Val Glu Arg Val Arg Asn Gly Glu Asn Pro Glu Leu Thr
                180                 185                 190

Thr Arg Glu Lys His Ala Arg Glu Cys Trp Val Val Leu Glu Glu Gly
            195                 200                 205

Ala Asp Ala Pro Lys Val Glu Gln Glu Ile Val Thr Met Pro Asn Tyr
210                 215                 220

Phe Asp Glu Tyr Asn Thr Thr Val Asn Phe Ile Ser Glu Asp Glu Phe
225                 230                 235                 240

Asn Ala Asn His Thr Gly Met Pro His Gly Gly Phe Val Ile Arg Ser
                245                 250                 255

Gly Glu Ser Gly Ala Asn Asp Lys Gln Ile Leu Glu Phe Ser Leu Lys
                260                 265                 270

Leu Glu Ser Asn Pro Asn Phe Thr Ser Ser Val Leu Val Ala Tyr Ala
            275                 280                 285

Arg Ala Ala His Arg Leu Ser Gln Ala Gly Glu Lys Gly Ala Lys Thr
        290                 295                 300

Val Phe Asp Ile Pro Phe Gly Leu Leu Ser Pro Lys Ser Ala Ala Gln
305                 310                 315                 320

Leu Arg Lys Glu Leu Leu
                325

<210> SEQ ID NO 4
<211> LENGTH: 320
<212> TYPE: PRT
<213> ORGANISM: Corynebacterium glutamicum

<400> SEQUENCE: 4

Met Thr Asn Ile Arg Val Ala Ile Val Gly Tyr Gly Asn Leu Gly Arg
1               5                   10                  15

Ser Val Glu Lys Leu Ile Ala Lys Gln Pro Asp Met Asp Leu Val Gly
                20                  25                  30

Ile Phe Ser Arg Arg Ala Thr Leu Asp Thr Lys Thr Pro Val Phe Asp
            35                  40                  45

Val Ala Asp Val Asp Lys His Ala Asp Asp Val Asp Val Leu Phe Leu
        50                  55                  60

Cys Met Gly Ser Ala Thr Asp Ile Pro Glu Gln Ala Pro Lys Phe Ala
65                  70                  75                  80

Gln Phe Ala Cys Thr Val Asp Thr Tyr Asp Asn His Arg Asp Ile Pro
                85                  90                  95

Arg His Arg Gln Val Met Asn Glu Ala Ala Thr Ala Ala Gly Asn Val
            100                 105                 110
```

```
Ala Leu Val Ser Thr Gly Trp Asp Pro Gly Met Phe Ser Ile Asn Arg
            115                 120                 125

Val Tyr Ala Ala Val Leu Ala Glu His Gln Gln His Thr Phe Trp
130                 135                 140

Gly Pro Gly Leu Ser Gln Gly His Ser Asp Ala Leu Arg Arg Ile Pro
145                 150                 155                 160

Gly Val Gln Lys Ala Val Gln Tyr Thr Leu Pro Ser Glu Asp Ala Leu
                165                 170                 175

Glu Lys Ala Arg Arg Gly Glu Ala Gly Asp Leu Thr Gly Lys Gln Thr
            180                 185                 190

His Lys Arg Gln Cys Phe Val Val Ala Asp Ala Ala Asp His Glu Arg
        195                 200                 205

Ile Glu Asn Asp Ile Arg Thr Met Pro Asp Tyr Phe Val Gly Tyr Glu
210                 215                 220

Val Glu Val Asn Phe Ile Asp Glu Ala Thr Phe Asp Ser Glu His Thr
225                 230                 235                 240

Gly Met Pro His Gly Gly His Val Ile Thr Thr Gly Asp Thr Gly Gly
                245                 250                 255

Phe Asn His Thr Val Glu Tyr Ile Leu Lys Leu Asp Arg Asn Pro Asp
            260                 265                 270

Phe Thr Ala Ser Ser Gln Ile Ala Phe Gly Arg Ala Ala His Arg Met
        275                 280                 285

Lys Gln Gln Gly Gln Ser Gly Ala Phe Thr Val Leu Glu Val Ala Pro
    290                 295                 300

Tyr Leu Leu Ser Pro Glu Asn Leu Asp Asp Leu Ile Ala Arg Asp Val
305                 310                 315                 320

<210> SEQ ID NO 5
<211> LENGTH: 297
<212> TYPE: PRT
<213> ORGANISM: Symbiobacterium thermophilum

<400> SEQUENCE: 5

Met Asp Lys Leu Arg Val Ala Val Val Gly Tyr Gly Asn Val Gly Arg
1               5                   10                  15

Tyr Ala Leu Glu Ala Val Gln Ala Ala Pro Asp Met Glu Leu Val Gly
            20                  25                  30

Val Val Arg Arg Lys Val Leu Ala Thr Pro Pro Glu Leu Thr Gly
        35                  40                  45

Val Arg Val Val Thr Asp Ile Ser Gln Leu Glu Gly Val Gln Gly Ala
50                  55                  60

Leu Leu Cys Val Pro Thr Arg Ser Val Pro Glu Tyr Ala Glu Ala Met
65                  70                  75                  80

Leu Arg Arg Gly Ile His Thr Val Asp Ser Tyr Asp Ile His Gly Asp
                85                  90                  95

Leu Ala Asp Leu Arg Arg Arg Leu Asp Pro Val Ala Arg Glu His Gly
            100                 105                 110

Ala Ala Ala Val Ile Ser Ala Gly Trp Asp Pro Gly Thr Asp Ser Ile
        115                 120                 125

Ile Arg Ala Leu Leu Glu Phe Met Ala Pro Lys Gly Ile Thr Tyr Thr
130                 135                 140

Asn Phe Gly Pro Gly Met Ser Met Gly His Ser Val Ala Val Lys Ala
145                 150                 155                 160

Ile Pro Gly Val Arg Asp Ala Leu Ser Met Thr Ile Pro Ala Gly Met
                165                 170                 175
```

```
Gly Val His Lys Arg Ala Val Tyr Val Glu Leu Pro Gly Ala Asp
            180                 185                 190

Phe Ala Glu Val Glu Arg Ala Ile Lys Thr Asp Pro Tyr Phe Val Arg
            195                 200                 205

Asp Glu Thr Arg Val Thr Gln Val Glu Ser Val Ser Ala Leu Met Asp
        210                 215                 220

Val Gly His Gly Val Val Met Glu Arg Lys Gly Val Ser Gly Ala Thr
225                 230                 235                 240

His Asn Gln Leu Phe Arg Phe Glu Met Arg Ile Asn Asn Pro Ala Leu
                245                 250                 255

Thr Ala Gln Val Met Val Ala Ala Leu Arg Ala Ala Arg Pro Gly
            260                 265                 270

Cys Tyr Thr Met Ile Glu Ile Pro Val Ile Asp Tyr Leu Pro Gly Asp
            275                 280                 285

Arg Glu Ala Trp Ile Arg Lys Leu Val
        290                 295

<210> SEQ ID NO 6
<211> LENGTH: 326
<212> TYPE: PRT
<213> ORGANISM: Ureibacillus thermosphaericus

<400> SEQUENCE: 6

Met Ser Lys Ile Arg Ile Gly Ile Val Gly Tyr Gly Asn Leu Gly Arg
1               5                   10                  15

Gly Val Glu Ala Ala Ile Gln Gln Asn Pro Asp Met Glu Leu Val Ala
            20                  25                  30

Val Phe Thr Arg Arg Asp Pro Lys Thr Val Ala Val Lys Ser Asn Val
        35                  40                  45

Lys Val Leu His Val Asp Asp Ala Gln Ser Tyr Lys Asp Glu Ile Asp
    50                  55                  60

Val Met Ile Leu Cys Gly Gly Ser Ala Thr Asp Leu Pro Glu Gln Gly
65                  70                  75                  80

Pro Tyr Phe Ala Gln Tyr Phe Asn Thr Ile Asp Ser Phe Asp Thr His
                85                  90                  95

Ala Arg Ile Pro Asp Tyr Phe Asp Ala Val Asn Ala Ala Glu Gln
            100                 105                 110

Ser Gly Lys Val Ala Ile Ile Ser Val Gly Trp Asp Pro Gly Leu Phe
        115                 120                 125

Ser Leu Asn Arg Leu Leu Gly Glu Val Val Leu Pro Val Gly Asn Thr
    130                 135                 140

Tyr Thr Phe Trp Gly Lys Gly Val Ser Gln Gly His Ser Asp Ala Ile
145                 150                 155                 160

Arg Arg Ile Gln Gly Val Lys Asn Ala Val Gln Tyr Thr Ile Pro Ile
                165                 170                 175

Asp Glu Ala Val Asn Arg Val Arg Ser Gly Glu Asn Pro Glu Leu Ser
            180                 185                 190

Thr Arg Glu Lys His Ala Arg Glu Cys Phe Val Val Leu Glu Glu Gly
        195                 200                 205

Ala Asp Pro Ala Lys Val Glu His Glu Ile Lys Thr Met Pro Asn Tyr
    210                 215                 220

Phe Asp Glu Tyr Asp Thr Thr Val His Phe Ile Ser Glu Glu Glu Leu
225                 230                 235                 240

Lys Gln Asn His Ser Gly Met Pro His Gly Gly Phe Val Ile Arg Ser
```

```
                        245                 250                 255
Gly Lys Ser Asp Glu Gly His Lys Gln Ile Ile Glu Phe Ser Leu Asn
            260                 265                 270

Leu Glu Ser Asn Pro Met Phe Thr Ser Ser Ala Leu Val Ala Tyr Ala
        275                 280                 285

Arg Ala Ala Tyr Arg Leu Ser Gln Asn Gly Asp Lys Gly Ala Lys Thr
    290                 295                 300

Val Phe Asp Ile Pro Phe Gly Leu Leu Ser Pro Lys Ser Pro Glu Asp
305                 310                 315                 320

Leu Arg Lys Glu Leu Leu
                325

<210> SEQ ID NO 7
<211> LENGTH: 918
<212> TYPE: DNA
<213> ORGANISM: Numidum massiliense

<400> SEQUENCE: 7
catatgagta atgtatacaa cgtcgccgtc gtcggctatg gtaatatcgg caagtacgcc      60
gtgcaagcaa tcgatgctgc tccggacatg caattagccg gtgtcgtcag acgcgcgagc     120
tccgccgcga agatacgcc gccagaactc gtcggacgcc gtgtcgtcca cgacatccgc      180
gacttggagc aagtcgacgt cgccatctta gcggcaccga cgcggacgat tccggcgtac     240
gcccgggacg ttctctcct cggcattcac acggtcgaca gttacgacat tcacggcgaa      300
ctcgctaact tgcggcgcga gttagacgat gtgtctaaaa aaaacgacag cgtcgccatc     360
atttccgcag gctgggatcc gggaaccgac tcgatgattc gcggcatgct cgagtttatg     420
gcgccaggtg ggttaacgta tacgaatttt gggcccggta tgagtatggg gcactccgtc     480
gccgtcaaag cgatcgacgg ggtcaaagac gcgctgtcct tgattatccc gctcggtacg     540
agcatccacc ggatgatggt gtacgtcgaa ctagaagcag gtgccgattt cgaaacggtc     600
aaaaaggcaa ttttagcaga tccgtatttc gtcaacgacg agactcatgt gacgcaagtt     660
cctaacgtac agcaactcgt caacgtcggt aacggagtct ccatggaacg gagaggcgta     720
tccggggcga cgcacaacca actgttcacg ttcgagatgc gcattaacaa cccggcactg     780
acgtcgcaag tgctcgtcgc cgctgcccgc gcgacgttca acagcaacc gggtgcgtac     840 acgatgatcg aggtaccggt aatcgattat ctccctggcg accgggacga cattattcgg     900
cggttagtgt aagaattc                                                   918

<210> SEQ ID NO 8
<211> LENGTH: 302
<212> TYPE: PRT
<213> ORGANISM: Numidum massiliense

<400> SEQUENCE: 8

Met Ser Asn Val Tyr Asn Val Ala Val Val Gly Tyr Gly Asn Ile Gly
1               5                   10                  15

Lys Tyr Ala Val Gln Ala Ile Asp Ala Ala Pro Asp Met Gln Leu Ala
            20                  25                  30

Gly Val Val Arg Arg Ala Ser Ser Ala Ala Lys Asp Thr Pro Pro Glu
        35                  40                  45

Leu Val Gly Arg Arg Val Val His Asp Ile Arg Asp Leu Glu Gln Val
    50                  55                  60

Asp Val Ala Ile Leu Ala Ala Pro Thr Arg Thr Ile Pro Ala Tyr Ala
65                  70                  75                  80
```

```
Arg Asp Val Leu Ser Leu Gly Ile His Thr Val Ser Tyr Asp Ile
                85                  90                  95

His Gly Glu Leu Ala Asn Leu Arg Arg Glu Leu Asp Asp Val Ser Lys
            100                 105                 110

Lys Asn Asp Ser Val Ala Ile Ile Ser Ala Gly Trp Asp Pro Gly Thr
        115                 120                 125

Asp Ser Met Ile Arg Gly Met Leu Glu Phe Met Ala Pro Gly Gly Leu
    130                 135                 140

Thr Tyr Thr Asn Phe Gly Pro Gly Met Ser Met Gly His Ser Val Ala
145                 150                 155                 160

Val Lys Ala Ile Asp Gly Val Lys Asp Ala Leu Ser Leu Ile Ile Pro
                165                 170                 175

Leu Gly Thr Ser Ile His Arg Met Met Val Tyr Val Glu Leu Glu Ala
            180                 185                 190

Gly Ala Asp Phe Glu Thr Val Lys Lys Ala Ile Leu Ala Asp Pro Tyr
        195                 200                 205

Phe Val Asn Asp Glu Thr His Val Thr Gln Val Pro Asn Val Gln Gln
    210                 215                 220

Leu Val Asn Val Gly Asn Gly Val Ser Met Glu Arg Arg Gly Val Ser
225                 230                 235                 240

Gly Ala Thr His Asn Gln Leu Phe Thr Phe Glu Met Arg Ile Asn Asn
                245                 250                 255

Pro Ala Leu Thr Ser Gln Val Leu Val Ala Ala Arg Ala Thr Phe
            260                 265                 270

Lys Gln Gln Pro Gly Ala Tyr Thr Met Ile Glu Val Pro Val Ile Asp
        275                 280                 285

Tyr Leu Pro Gly Asp Arg Asp Asp Ile Ile Arg Arg Leu Val
    290                 295                 300

<210> SEQ ID NO 9
<211> LENGTH: 918
<212> TYPE: DNA
<213> ORGANISM: Numidum massiliense

<400> SEQUENCE: 9
catatgagta atgtatacaa cgtcgccgtc gtcggctatg gtaatatcgg caagtacgcc        60
gtgcaagcaa tcgatgctgc tccggacatg caattagccg tgtcgtcag acgcgcgagc       120
tccgccgcga agatacgcc gccagaactc gtcggacgcc gtgtcgtcca cgacatccgc       180
gacttggagc aagtcgacgt cgccatctta gcggcaccga cgcggacgat tccggcgtac       240
gcccgggacg ttctctcct cggcattcac acggtcgaca gttactccat tcacggcgaa       300
ctcgctaact gcggcgcga gttagacgat gtgtctaaaa aaaacgacag cgtcgccatc       360
atttccgcag gctgggatcc gggaaccgac tcgatgattc gcggcatgct cgagtttatg       420
gcgccaggtg ggttaacgta tacgaatttt gggcccggta tgagtttagg cactccggt       480
gccgtcaaag cgatcgacgg ggtcaaagac gcgctgtcct tgattatccc gctcggtacg       540
agcatccacc ggatgatggt gtacgtcgaa ctagaagcag gtgccgattt cgaaacggtc       600
aaaaaggcaa ttttagcaga tccgtatttc gtcaacgacg agactcatgt gacgcaagtt       660
cctaacgtac agcaactcgt caacgtcggt aacggagtct ccatggaacg gagaggcgta       720
tccggggcga cgcacaacca actgttcacg ttcgagatgc gcattaacaa cccggcactg       780
acgtcgcaag tgctcgtcgc cgctgcccgc gcgacgttca acagcaaacc gggtgcgtac       840
```
acgatgatcg aggtaccggt aatcgattat ctccctggcg accgggacga cattattcgg    900
cggttagtgt aagaattc    918

<210> SEQ ID NO 10
<211> LENGTH: 302
<212> TYPE: PRT
<213> ORGANISM: Numidum massiliense

<400> SEQUENCE: 10

Met Ser Asn Val Tyr Asn Val Ala Val Val Gly Tyr Gly Asn Ile Gly
1               5                   10                  15

Lys Tyr Ala Val Gln Ala Ile Asp Ala Ala Pro Asp Met Gln Leu Ala
            20                  25                  30

Gly Val Val Arg Arg Ala Ser Ser Ala Ala Lys Asp Thr Pro Pro Glu
        35                  40                  45

Leu Val Gly Arg Arg Val Val His Asp Ile Arg Asp Leu Glu Gln Val
    50                  55                  60

Asp Val Ala Ile Leu Ala Ala Pro Thr Arg Thr Ile Pro Ala Tyr Ala
65                  70                  75                  80

Arg Asp Val Leu Ser Leu Gly Ile His Thr Val Asp Ser Tyr Ser Ile
                85                  90                  95

His Gly Glu Leu Ala Asn Leu Arg Arg Glu Leu Asp Asp Val Ser Lys
            100                 105                 110

Lys Asn Asp Ser Val Ala Ile Ile Ser Ala Gly Trp Asp Pro Gly Thr
        115                 120                 125

Asp Ser Met Ile Arg Gly Met Leu Glu Phe Met Ala Pro Gly Gly Leu
    130                 135                 140

Thr Tyr Thr Asn Phe Gly Pro Gly Met Ser Leu Gly His Ser Gly Ala
145                 150                 155                 160

Val Lys Ala Ile Asp Gly Val Lys Asp Ala Leu Ser Leu Ile Ile Pro
                165                 170                 175

Leu Gly Thr Ser Ile His Arg Met Met Val Tyr Val Glu Leu Glu Ala
            180                 185                 190

Gly Ala Asp Phe Glu Thr Val Lys Lys Ala Ile Leu Ala Asp Pro Tyr
        195                 200                 205

Phe Val Asn Asp Glu Thr His Val Thr Gln Val Pro Asn Val Gln Gln
    210                 215                 220

Leu Val Asn Val Gly Asn Gly Val Ser Met Glu Arg Arg Gly Val Ser
225                 230                 235                 240

Gly Ala Thr His Asn Gln Leu Phe Thr Phe Glu Met Arg Ile Asn Asn
                245                 250                 255

Pro Ala Leu Thr Ser Gln Val Leu Val Ala Ala Arg Ala Thr Phe
            260                 265                 270

Lys Gln Gln Pro Gly Ala Tyr Thr Met Ile Glu Val Pro Val Ile Asp
        275                 280                 285

Tyr Leu Pro Gly Asp Arg Asp Asp Ile Ile Arg Arg Leu Val
    290                 295                 300

<210> SEQ ID NO 11
<211> LENGTH: 30
<212> TYPE: DNA
<213> ORGANISM: artificial
<220> FEATURE:
<223> OTHER INFORMATION: primer

<400> SEQUENCE: 11

```
cggtcgacag ttacgacatt cacggcgaac                                      30
```

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12

```
gttcgccgtg aatgtcgtaa ctgtcgaccg                                      30
```

<210> SEQ ID NO 13
<211> LENGTH: 918
<212> TYPE: DNA
<213> ORGANISM: Numidum massiliense

<400> SEQUENCE: 13

```
catatgagta atgtatacaa cgtcgccgtc gtcggctatg gtaatatcgg caagtacgcc     60
gtgcaagcaa tcgatgctgc tccggacatg caattagccg gtgtcgtcag acgcgcgagc   120
tccgccgcga agatacgcc gccagaactc gtcggacgcc gtgtcgtcca cgacatccgc    180
gacttggagc aagtcgacgt cgccatctta gcggcaccga cgcggacgat tccggcgtac   240
gcccgggacg ttctctcccct cggcattcac acggtcgaca gttacgacat tcacggcgaa  300
ctcgctaact tgcggcgcga gttagacgat gtgtctaaaa aaacgacag cgtcgccatc    360
atttccgcag gctgggatcc gggaaccgac tcgatgattc gcggcatgct cgagtttatg   420
gcgccaggtg ggttaacgta tacgaatttt gggcccggta tgagtttagg cactccggt   480
gccgtcaaag cgatcgacgg ggtcaaagac gcgctgtcct tgattatccc gctcggtacg   540
agcatccacc ggatgatggt gtacgtcgaa ctagaagcag gtgccgattt cgaaacggtc   600
aaaaaggcaa ttttagcaga tccgtatttc gtcaacgacg agactcatgt gacgcaagtt   660
cctaacgtac agcaactcgt caacgtcggt aacggagtct ccatggaacg gagaggcgta   720
tccggggcga cgcacaacca actgttcacg ttcgagatgc gcattaacaa cccggcactg   780
acgtcgcaag tgctcgtcgc cgctgcccgc gcgacgttca acagcaacc gggtgcgtac   840
acgatgatcg aggtaccggt aatcgattat ctccctggcg accgggacga cattattcgg   900
cggttagtgt aagaattc                                                  918
```

<210> SEQ ID NO 14
<211> LENGTH: 302
<212> TYPE: PRT
<213> ORGANISM: Numidum massiliense

<400> SEQUENCE: 14

```
Met Ser Asn Val Tyr Asn Val Ala Val Val Gly Tyr Gly Asn Ile Gly
 1               5                  10                  15

Lys Tyr Ala Val Gln Ala Ile Asp Ala Ala Pro Asp Met Gln Leu Ala
                20                  25                  30

Gly Val Val Arg Arg Ala Ser Ser Ala Ala Lys Asp Thr Pro Pro Glu
            35                  40                  45

Leu Val Gly Arg Arg Val Val His Asp Ile Arg Asp Leu Glu Gln Val
        50                  55                  60

Asp Val Ala Ile Leu Ala Ala Pro Thr Arg Thr Ile Pro Ala Tyr Ala
 65                 70                  75                  80

Arg Asp Val Leu Ser Leu Gly Ile His Thr Val Asp Ser Tyr Asp Ile
                85                  90                  95
```

-continued

```
His Gly Glu Leu Ala Asn Leu Arg Arg Glu Leu Asp Val Ser Lys
            100                 105             110

Lys Asn Asp Ser Val Ala Ile Ile Ser Ala Gly Trp Asp Pro Gly Thr
        115             120             125

Asp Ser Met Ile Arg Gly Met Leu Glu Phe Met Ala Pro Gly Gly Leu
    130             135             140

Thr Tyr Thr Asn Phe Gly Pro Gly Met Ser Leu Gly His Ser Gly Ala
145             150             155                 160

Val Lys Ala Ile Asp Gly Val Lys Asp Ala Leu Ser Leu Ile Ile Pro
                165             170                 175

Leu Gly Thr Ser Ile His Arg Met Met Val Tyr Val Glu Leu Glu Ala
            180             185             190

Gly Ala Asp Phe Glu Thr Val Lys Lys Ala Ile Leu Ala Asp Pro Tyr
        195             200             205

Phe Val Asn Asp Glu Thr His Val Thr Gln Val Pro Asn Val Gln Gln
        210             215             220

Leu Val Asn Val Gly Asn Gly Val Ser Met Glu Arg Arg Gly Val Ser
225             230             235                 240

Gly Ala Thr His Asn Gln Leu Phe Thr Phe Glu Met Arg Ile Asn Asn
                245             250             255

Pro Ala Leu Thr Ser Gln Val Leu Val Ala Ala Ala Arg Ala Thr Phe
            260             265             270

Lys Gln Gln Pro Gly Ala Tyr Thr Met Ile Glu Val Pro Val Ile Asp
        275             280             285

Tyr Leu Pro Gly Asp Arg Asp Asp Ile Ile Arg Arg Leu Val
290             295             300
```

D-TYPE AMINO ACID DEHYDROGENASE

TECHNICAL FIELD

There is disclosed a technique relating to a D-type amino acid dehydrogenase.

BACKGROUND ART

Proteins, which are one important component in the body, are mainly composed of 20 types of α-amino acids. Since 19 types among these have asymmetric carbon except for glycine, there are two optical isomers, D-type amino acid and L-type amino acid. Although it is known that most of the amino acids that form proteins are L-type amino acids, according to recent developments in analytical techniques, it has been clearly found that D-type amino acids are present in a trace amount in cells of higher organisms such as mammals including humans, aquatic animals, plants, and the like.

D-Type amino acids have broad industrial use as a raw material for the production of pharmaceuticals such as ovulation inducing agents, anticoagulants, and analgesics, and also as an intermediate of industrial products such as insecticides, antibiotics, and cosmetics. Therefore, there is a need for an efficient method for producing D-type amino acid.

SUMMARY OF INVENTION

Technical Problem

An object is to provide a technique for efficient production of D-type amino acid.

Solution to Problem

In order to achieve this object, as a result of repeated intensive studies, there is provided the invention represented below.

Aspect 1

An enzyme having the following characteristics of (a) and (b):
(a) the enzyme has an activity of reversible dehydrogenation of D-amino acid; and
(b) the enzyme is a hexamer of polypeptides having an amino acid sequence that has 80% or greater identity with an amino acid sequence of SEQ ID NO: 2.

Aspect 2

The enzyme according to Aspect 1, further having an activity of synthesizing D-aspartic acid from 2-oxobutanedioic acid.

Aspect 3

The enzyme according to Aspect 1 or 2, further having the following characteristic (c):
(c) the enzyme is capable of utilizing both NADH and NADPH as coenzymes.

Aspect 4

The enzyme according to any one of Aspects 1 to 3, further having the following characteristic (d):
(d) the enzyme has a $k_{cat}$ of $1.0 \times 10^4$ min$^{-1}$ or greater in a case of using meso-diaminopimelic acid as a substrate.

Aspect 5

The enzyme according to any one of Aspects 1 to 4, further having the following characteristic (e):
(e) the enzyme has an optimum pH for activity of 10.5 in a case of using meso-diaminopimelic acid as the substrate.

Aspect 6

The enzyme according to any one of Aspects 1 to 5, further having the following characteristic (f):
(f) the enzyme has an optimum temperature for activity of 75° C. in a case of using the meso-diaminopimelic acid as the substrate.

Aspect 7

The enzyme according to Aspect 1 or 2,
wherein in the amino acid sequence that has 80% or greater identity with the amino acid sequence of SEQ ID NO: 2, the enzyme contains one or more amino acid substitutions selected from the group consisting of Asp95Ser, Met155Leu, Val159Gly, Thr174Ile, Arg184Met, and His230Asn.

Aspect 8

Polynucleotide encoding the enzyme described in any one of Aspects 1 to 7.

Aspect 9

A vector including the polynucleotide described in Aspect 8.

Aspect 10

A transformant containing the vector described in Aspect 9.

Aspect 11

A method for producing the enzyme described in any one of Aspects 1 to 7 including culturing the transformant described in Aspect 10.

Aspect 12

A method for producing D-amino acid including allowing the enzyme described in any one of Aspects 1 to 7 to act on 2-oxo acid.

Advantageous Effects of Invention

It is possible to efficiently synthesize D-type amino acid and/or 2-oxo acid.

BRIEF DESCRIPTION OF THE DRAWINGS

FIG. 1 illustrates a base sequence of DNA encoding a D-type amino acid dehydrogenase derived from *N. massiliense*. Underlines are restriction enzyme recognition sites for cloning, and bolds are stop codons.

FIG. 2 illustrates an amino acid sequence of a D-type amino acid dehydrogenase derived from *N. massiliense*.

FIG. 3 illustrates a result of SDS-PAGE of a crude enzyme solution, a heat-treated enzyme solution, and active fractions obtained after various chromatographies and a molecular weight marker. Lane 1 is the result of the molecular weight marker, lane 2 is the crude enzyme solution, lane 3 is the heat-treated crude enzyme solution, lane 4 is an active fraction after TOYOPEARL SuperQ-650 anion exchange chromatography, lane 5 is an active fraction after Butyl-650M hydrophobic chromatography, and lane 6 is an active fraction after Superdex200 gel filtration chromatography.

FIG. 4 illustrates the results of protein staining and activity-staining of a purified enzyme. Lane 1 indicates the result of the protein staining, lane 2 indicates the result of the activity-staining with NAD$^+$ for coenzyme, and lane 3 indicates the result of the activity-staining with NADP$^+$.

FIG. 12 illustrates a base sequence of DNA encoding an amino acid sequence obtained by substituting three amino acid residues of the D-type amino acid dehydrogenase derived from *N. massiliense*. Squares are mutation-introduced sites, underlines are restriction enzyme recognition sites for cloning, and bolds are stop codons.

FIG. 13 illustrates an amino acid sequence obtained by substituting three amino acid residues of the D-type amino acid dehydrogenase derived from *N. massiliense*. Squares are the mutation-introduced sites.

FIG. 14 illustrates a base sequence of DNA encoding an amino acid sequence obtained by substituting six amino acid residues of the D-type amino acid dehydrogenase derived from *N. massiliense*. Squares are mutation-introduced sites, underlines are restriction enzyme recognition sites for cloning, and bolds are stop codons.

FIG. 15 illustrates an amino acid sequence obtained by substituting six amino acid residues of the D-type amino acid dehydrogenase derived from *N. massiliense*. Squares are the mutation-introduced sites.

FIG. 16 illustrates a base sequence of DNA encoding an amino acid sequence obtained by substituting five amino acid residues of the D-type amino acid dehydrogenase derived from *N. massiliense*. Squares are mutation-introduced sites, underlines are restriction enzyme recognition sites for cloning, and bolds are stop codons.

FIG. 17 illustrates an amino acid sequence obtained by substituting five amino acid residues of the D-type amino acid dehydrogenase derived from *N. massiliense*.

FIG. 18 illustrates the results of protein staining and activity-staining of a purified D-type amino acid dehydrogenase. Lane 1 indicates the result of the protein staining, lane 2 indicates the result of the activity-staining with D-alanine for a substrate, and lane 3 indicates the result of the activity-staining with L-alanine for a substrate.

DESCRIPTION OF EMBODIMENTS

Figure 5:
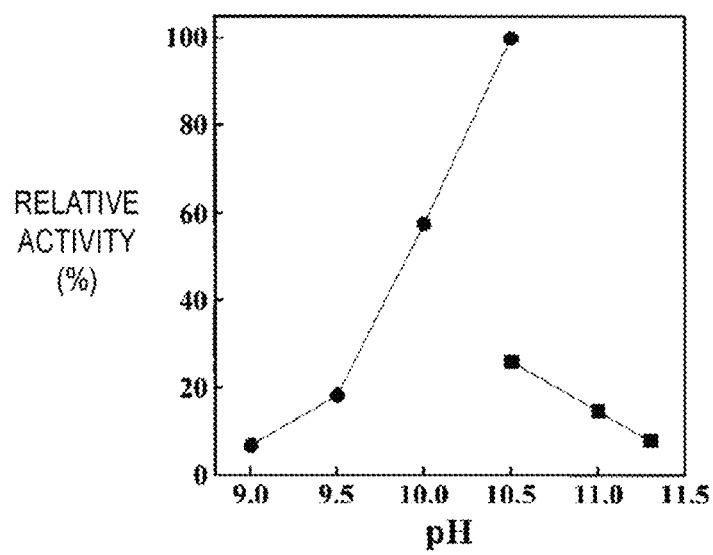
FIG. 5 illustrates a result of measurement of pH dependence of the enzyme in a deamination reaction of meso-diaminopimelic acid. Specific activity in a glycine buffer solution (pH 10.5) was calculated as 100% to calculate a relative activity at each pH. A horizontal axis indicates pH for measurement (pH) and a vertical axis indicates relative activity (%). ● represents a glycine buffer solution, and ■ represents a carbonate buffer solution, respectively.

An enzyme preferably has an activity of reversible dehydrogenation of D-type amino acid. Note that the D-type amino acid herein is also referred to as "D-amino acid" or "D amino acid". A D-type amino acid is an optical isomer of an amino acid having asymmetric carbon. The D-type amino acid herein also includes meso type amino acid (such as meso-diaminopimelic acid) having a structure of both L and D in a molecule. In one embodiment, the D-type amino acid is not a meso-type (substantially free of L-type).

Reversible dehydrogenation of the D-type amino acid means that both a reaction of converting the D-type amino acid into corresponding oxo acid and a reaction of converting the oxo acid to corresponding D-type amino acid are catalyzed. The reaction is represented by the following formula:

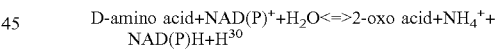

D-amino acid+NAD(P)$^+$+H$_2$O<=>2-oxo acid+NH$_4^+$+ NAD(P)H+H$^{30}$

For example, in a case where the D-type amino acid is meso-diaminopimelic acid, the reaction of converting meso-diaminopimelic acid to L-2-amino-6-oxopimelic acid and the reaction of converting L-2-amino-6-oxopimelic acid to meso-diaminopimelic acid are catalyzed. Such an enzyme can also be referred to as "meso-diaminopimelic acid dehydrogenase". In one embodiment, the enzyme preferably has at least an activity of catalyzing the conversion of the oxo acid to the D-type amino acid. That is, in one embodiment, the enzyme is not necessary to have the activity of converting the D-type amino acid to the oxo acid.

The enzyme preferably has the amino acid sequence of SEQ ID NO: 2 or an amino acid sequence having identity of 60% or greater, 65% or greater, 70% or greater, 75% or greater, 80% or greater, 85% or greater, 90%, 91% or greater, 92% or greater, 93% or greater, 94% or greater, 95% or greater, 96% or greater, 97% or greater, 98% or greater, and 99% or greater with the amino acid sequence of SEQ ID NO: 2. SEQ ID NO: 2 is an amino acid sequence of the D-type amino acid dehydrogenase derived from *Numidum massiliense*.

The identity of amino acid can be calculated using analytical tools (for example, software such as FASTA, BLAST, PSI-BLAST, and SSEARCH) that are commercially available or available through the Internet. For example, in Advanced BLAST 2.1, using blastp for a program, Expect value is set as 10, and Filters are all set to OFF, using BLOSUM62 for Matrix, Gap existence cost, Per residue gap cost, and Lambda ratio are respectively set to be 11, 1, and 0.85 (default values), and the other parameters are set to default values, and search is conducted to calculate an identity value (%) of the amino acid sequence.

The enzyme preferably has one or more amino acid residues selected from the group consisting of the 6th to 17th, 19th, 23rd, 27th to 35th, 37th, 48th, 54th, 62nd, 64th, 65th, 68th to 70th, 73rd, 75th, 84th, 90th to 95th, 97th, 100th, 107th, 108th, 110th, 111st, 115th, 117th to 127th, 130th, 131st, 133rd, 139th, 146th, 147th, 149th, 150th, 152nd to 158th, 160th to 162nd, 164th, 166th to 172nd, 174th to 176th, 182nd, 184th, 187th, 188th, 191st, 193rd to 195th, 199th to 201st, 203rd, 205th, 207th, 209th, 213rd, 214th, 216th, 219th, 227th, 228th, 230th, 231st, 234th, 238th, 240th, 241st, 245th, 246th, 248th, 250th, 252nd to 254th, 256th, 257th, 259th to 262nd, 265th, 266th, 269th, 270th, 271st, 273rd, 275th, 277th, 278th, 280th to 284th, 291st, 293rd, 300th, and 302nd amino acid residues in the amino acid sequence of SEQ ID NO: 2. Here, "one or more amino acid residues" is preferably, for example, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more, 105 or more, 110 or more, 115 or more, 120 or more, 125 or more, 130 or more, 135 or more, 140 or more, or 145 amino acid residues.

In one embodiment, the enzyme preferably has one or more amino acid residues selected from the group consisting of the 10th to 14th, 16th, 27th to 29th, 31st, 37th, 54th, 69th, 90th, 92nd, 95th, 97th, 121st, 123rd to 127th, 130th, 133rd, 147th, 150th, 152nd, 154th, 156th, 158th, 160th, 164th, 166th, 167th, 170th, 174th, 176th, 182nd, 184th, 188th, 194th, 195th, 203rd, 207th, 209th, 216th, 230th, 231st, 238th, 256th, 257th, 260th, 266th, 270th, 271st, 277th, 280th, and 291st amino acid residues in the amino acid sequence of SEQ ID NO: 2. Herein, "one or more amino acid residues" may be 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, or 60 amino acid residues. In one embodiment, it is preferable to have more amino acid residues other than the specific amino acid residues above.

In one preferable embodiment, the enzyme preferably further has one or more amino acid residues selected from the group consisting of the 7th, 9th, 15th, 17th, 23rd, 30th, 34th, 48th, 62nd, 64th, 65th, 68th, 73rd, 75th, 84th, 91st, 93rd, 94th, 100th, 107th, 108th, 111st, 118th to 120th, 131st, 139th, 146th, 149th, 153rd, 161st, 162nd, 168th, 171st, 175th, 187th, 191st, 199th, 200th, 205th, 213rd, 219th, 228th, 240th, 245th, 246th, 250th, 252nd, 254th, 259th, 261st, 265th, 271st, 273rd, 281st to 284th, and 302nd amino acid residues in the amino acid sequence of SEQ ID NO: 2. Herein, "one or more amino acid residues" may be 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, or 60 amino acid residues. In one embodiment, it is preferable to have more amino acid residues other than the specific amino acid residues above.

In one more preferable embodiment, the enzyme preferably further has one or more amino acid residues selected from the group consisting of the 6th, 8th, 19th, 32nd, 33rd, 70th, 110th, 117th, 122nd, 169th, 172nd, 193rd, 201st, 214th, 227th, 241st, 248th, 253rd, 262nd, 275th, 278th, 293rd, and 300th amino acid residues in the amino acid sequence of SEQ ID NO: 2. Herein, "one or more amino acid residues" may be 1 or more, 2 or more, 3 or more, 4 or more, 5 or more, 6 or more, 7 or more, 8 or more, 9 or more, 10 or more, 15 or more, 20 or more, or 25 amino acid residues.

In one embodiment, the enzyme may have one or more substitutions of the amino acid residues in Table 1 below in the amino acid sequence of SEQ ID NO: 2. Herein, "one or more" may be 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, or 85.

TABLE 1

| Position | Substituted amino acid residue |
|---|---|
| 6 | R |
| 7 | I |
| 8 | G |
| 9 | I |
| 15 | V, L |
| 17 | R |
| 19 | V |
| 23 | V |
| 30 | E, D |
| 32 | V |
| 33 | A |
| 34 | I |
| 35 | F |
| 48 | K, N |
| 62 | D |
| 64 | I |
| 65 | Q |
| 68 | F, L |
| 70 | C |
| 73 | S |
| 75 | S |
| 84 | F |
| 91 | I |
| 93 | T |
| 94 | F |
| 100 | I |
| 107 | V, M |
| 108 | N |
| 110 | A |
| 111 | A |
| 115 | G |
| 117 | A |
| 118 | S |
| 119 | V |
| 120 | V |
| 122 | T, V |
| 131 | I, L |
| 139 | V |
| 146 | H |
| 149 | W |
| 153 | V |
| 161 | L, I |
| 162 | R |
| 168 | Q, R |
| 169 | K, N |
| 171 | V |
| 172 | Q |

TABLE 1-continued

| Position | Substituted amino acid residue |
|---|---|
| 175 | L |
| 187 | W, F |
| 191 | D |
| 193 | A |
| 199 | I |
| 200 | E |
| 201 | Q, N, R, H |
| 205 | T |
| 213 | N, D |
| 214 | V |
| 219 | I |
| 227 | G, D |
| 228 | M |
| 234 | V |
| 240 | T |
| 241 | D |
| 245 | K |
| 246 | H |
| 248 | V, I |
| 250 | Y |
| 252 | L |
| 253 | K, N |
| 254 | L |
| 259 | F |
| 261 | A |
| 262 | S |
| 265 | I |
| 271 | A |
| 273 | R |
| 275 | K |
| 278 | C |
| 281 | V |
| 282 | L, F |
| 283 | D |
| 284 | I |
| 293 | S, N |
| 300 | E, K |
| 302 | L |

In Table 1, "position" means the position of the amino acid residue in SEQ ID NO: 2. The "substituted amino acid residue" means a type of amino acid residue that can substitute for an amino acid residue at a specific position of SEQ ID NO: 2. In Table 1, the amino acid residue types are listed in alphabetical letters.

In one embodiment, the substitutions of the amino acid residues are preferably conservative amino acid substitutions. The "conservative amino acid substitution" means substitution of a certain amino acid residue with an amino acid residue having a side chain with similar property. The amino acid residues are classified into several families depending on the side chains thereof, namely, a basic side chain (such as lysine, arginine, and histidine), an acidic side chain (such as aspartic acid and glutamic acid), an uncharged polar side chain (such as glycine, asparagine, glutamine, serine, threonine, tyrosine, and cysteine), a nonpolar side chain (such as alanine, valine, leucine, isoleucine, proline, phenylalanine, methionine, and tryptophan), a β-branched side chain (such as threonine, valine, and isoleucine), and an aromatic side chain (such as tyrosine, phenylalanine, tryptophan, and histidine). Thus, substitution between amino acid residues within the same family is preferable.

In one embodiment, in the enzyme, preferably one or more amino acid residues selected from the group consisting of Asp95, Met155, Val159, Thr174, Arg184, and His230 in SEQ ID NO: 2 or an amino acid sequence having 80% or more identity thereof are substituted with other amino acid residues. In one embodiment, the enzyme preferably has substitutions of one or more amino acid residues selected from the group consisting of Asp95Ser, Met155Leu, Val159Gly, Thr174Ile, Arg184Met, and His230Asn in the SEQ ID NO: 2 or the amino acid sequence having 80% or more identity thereof. Here, "Met155Leu" means that the methionine residue at the 155th position is substituted with a leucine residue. The same applies to the other substitutions. Also, "one or more" may preferably be 2 or more, 3 or more, 4 or more, 5 or more, or 6. Substitutions of Thr174Ile, Arg184Met, and/or His230Asn allows for the production of oxo acid and D-amino acid corresponding to a wider variety of D-amino acids and 2-oxo acids as substrates. It is also possible to increase catalyst efficiency by substitutions of Asp95Ser, Met155Leu, and/or Val159Gly.

For example, in the SEQ ID NO: 2 or the amino acid sequence having 80% or more identity thereof, due to the substitutions of Thr174Ile, Arg184Met, and His230Asn, the enzyme has higher activity of catalyzing the following reactions than before mutation: reaction of converting 2-oxo-3-methylbutanoic acid into D-valine; reaction of converting 2-oxo-4-methylpentanoic acid into D-leucine acid; reaction of converting 2-oxo-3-methylpentanoic acid into D-isoleucine; reaction of converting 2-oxo-4-(methylthio) butanoic acid into D-methionine; reaction of converting 2-oxobutanoic acid into D-2-aminobutyric acid; and reaction of converting 2-oxooctanoic acid into D-2-aminooctanoic acid. Thus, in the SEQ ID NO: 2 or the amino acid sequence having 80% or more identity thereof, an enzyme having substitutions of Thr174Ile, Arg184Met, and His230Asn is suitable for the production of D-valine, D-leucine, D-isoleucine, D-methionine, D-2-aminobutyric acid, and D-2-aminooctanoic acid. Also, in the SEQ ID NO: 2 or the amino acid sequence having 80% or more identity thereof, due to not only the substitutions of Thr174Ile, Arg184Met, and His230Asn, but also Met155Leu and Val159Gly, the enzyme has higher activity of catalyzing the following reactions than before mutation: reaction of converting 2-oxo-4-methylpentanoic acid into D-leucine acid; reaction of converting 2-oxo-3-phenylpropanoic acid into D-phenylalanine; reaction of converting 2-oxo-4-(methylthio)butanoic acid into D-methionine; and reaction of converting 2-oxooctanoic acid into D-2-aminooctanoic acid.

On the other hand, in the SEQ ID NO: 2 or the amino acid sequence having 80% or more identity thereof, an enzyme without mutations of Asp95Ser, Met155Leu, Val159Gly, Thr174Ile, Arg184Met, and His230Asn has a relatively high activity of catalyzing the following reactions: reaction of converting 2-oxopropanoic acid into D-alanine, reaction of converting 2-oxobutanedioic acid into D-aspartic acid, and reaction of converting 2-oxoglutaric acid into D-glutamic acid. Thus, the enzyme without the specific mutations (substitutions) described above is suitable for the production of D-alanine, D-aspartic acid, and D-glutamic acid.

In one embodiment, the enzyme preferably has one or more amino acid residues selected from the group consisting of Asp95, Asp125, Met155, Gly156, Thr174, Arg184, and His230 in an amino acid sequence of the SEQ ID NO: 2. Also, "one or more" may preferably be 2 or more, 3 or more, 4 or more, 5 or more, 6 or more, or 7. It is considered that existence (maintenance) of the one or more amino acid residues suitably satisfies the characteristics of $k_{cat}(min^{-1})$ and the like described below.

The enzyme is preferably a hexamer. The fact that the enzyme is hexamer means a state where six polypeptides (monomers) form one integrated structure when the enzyme is active (in an active state). The hexamer may be either a homohexamer or a heterohexamer, and is preferably a homohexamer.

In one embodiment, the enzyme preferably has the activity of producing D-aspartic acid from 2-oxobutanedioic acid. Such an enzyme may or may not have mutations of Asp95Ser, Met155Leu, Val159Gly, Thr174Ile, Arg184Met, and His230Asn in the SEQ ID NO: 2 or the amino acid sequence having 80% or more identity thereof. In one embodiment, it is preferable that the enzyme does not have the mutations, from the viewpoint of producing more efficiently D-aspartic acid.

In one embodiment, the enzyme preferably has the activity of producing D-glutamic acid from 2-oxoglutaric acid. It is preferable that such an enzyme does not have mutations of Asp95Ser, Met155Leu, Val159Gly, Thr174Ile, Arg184Met, and His230Asn, in the SEQ ID NO: 2 or the amino acid sequence having 80% or greater identity thereof.

It is preferable that the enzyme is capable of utilizing both NADH and NADPH as coenzymes for catalyzing a reversible dehydrogenation reaction of the D-type amino acid. The NADH is generally less expensive than the NADPH. Thus, the availability of NADH as a coenzyme is meaningful for reducing costs of manufacturing, for example, D-type amino acid using an enzyme.

The enzyme preferably has a $k_{cat}$ (min$^{-1}$) of $1.0\times10^4$ or greater in a case of using meso-diaminopimelic acid as a substrate. $k_{cat}$(min$^{-1}$) is preferably $1.5\times10^4$, $2.0\times10^4$ or greater, $2.5\times10^4$ or greater, $3.0\times10^4$ or greater, $3.5\times10^4$ or greater, or $3.8\times10^4$ or greater. $k_{cat}$ is a parameter of amounts of substrates that can be catalyzed per unit time.

The enzyme preferably has a $K_m$ value of 4.0 mM or less, or 3.5 mM or less, in a case where meso-diaminopimelic acid is used as a substrate. The $K_m$ value is a parameter indicating the affinity between the enzyme and the substrate. The lower the value, the higher the affinity, and the desired reaction can be efficiently performed with a small amount of enzyme.

The enzyme preferably has a $K_m$ value of 1000 mM or less, 950 mM or less, or 900 mM or less for NAD$^+$ in a case where meso-diaminopimelic acid is used as a substrate, and NAD$^+$ is as a coenzyme. With such $K_m$ values, the amount of NAD$^+$ required to produce the D-amino acid or oxo acid using the enzyme can be reduced.

The enzyme preferably has a $K_m$ value of 10 mM or less, 1 mM or less, or 0.5 mM or less, for NADP$^+$ in a case where meso-diaminopimelic acid is used as a substrate, and NADP$^+$ is as a coenzyme. With such $K_m$ values, the amount of NADP$^+$ required to produce the D-amino acid or oxo acid using the enzyme can be reduced.

The enzyme preferably has an optimum pH for activity of 10.5 in a case of using meso-diaminopimelic acid as a substrate. The optimum pH for activity of 10.5 means that the enzymatic activity is high in a case where pH is 10.5 as compared to a case where pH is from 9.0 to 10.0 and from 11.0 to 11.5, as illustrated in FIG. 5.

Figure 6:
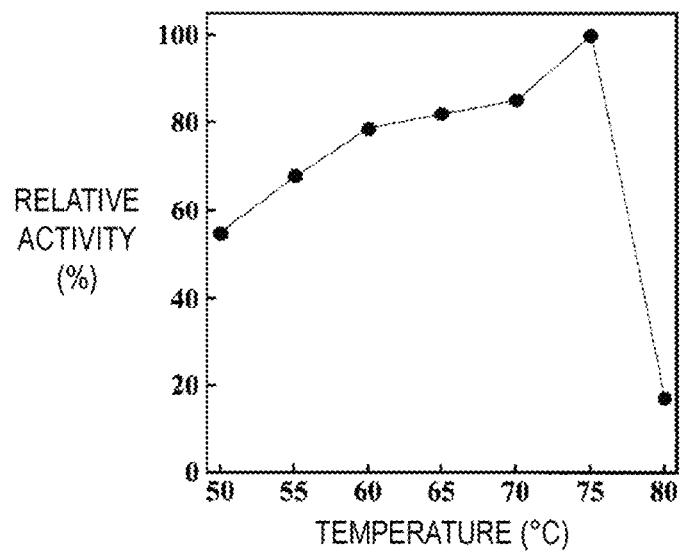
FIG. 6 illustrates a result of measurement of temperature dependence of the enzyme in the deamination reaction of meso-diaminopimelic acid. A horizontal axis indicates temperature for measurement (° C.) and a vertical axis indicates a relative activity (%).

The enzyme preferably has an optimum temperature for activity of 75° C. in a case of using meso-diaminopimelic acid as a substrate. The optimum temperature for activity of 75° C. means that the enzymatic activity at 75° C. is high as compared to the enzymatic activity at 50° C. to 70° C. and 80° C. as illustrated in FIG. 6.

In the enzyme, a molecular weight of a polypeptide moiety (monomer) thereof measured by SDS-PAGE is preferably about 32 kDa. "About 32 kDa" means to include a range where a person skilled in the art determines that a band is normally present at a position of 32 kDa when the molecular weight is measured by SDS-PAGE. The "polypeptide moiety" means polypeptide that is substantially unbound to a sugar chain.

The enzyme preferably has excellent thermal stability. For example, in the enzyme, the activity after 30 minutes of retention at 60° C. is preferably 75% or more as compared to the activity after 30 minutes of retention at 40° C. (meso-diaminopimelic acid as substrate).

The enzyme preferably has excellent pH stability. For example, the enzyme preferably has a residual activity after 30 minutes of retention in a buffer solution having pH of 5.5 to 9.5 is 90% or more as compared to the residual activity after 30 minutes of retention in a buffer solution having pH of 5.5. For example, the enzyme preferably has a residual activity after 30 minutes of retention in a buffer solution having pH of 5.5 to 13.0 is 80% or greater as compared to the residual activity after 30 minutes of retention in a buffer solution having pH of 5.5.

The source of the enzyme is not particularly limited. For example, the enzyme is preferably derived from microorganisms belonging to the genus *Numidum* (for example, *Numidum massiliense*).

The enzyme may be in a crystalline state. The enzyme in the crystalline state can be obtained, for example, according to the examples described below. The enzyme in the crystalline state is useful for purification in high purity, and stable storage and immobilization with high density and strong protease resistance.

The enzyme described above can be obtained by any method. For example, the enzyme can be obtained by utilizing a gene encoding a protein having an amino acid sequence represented in SEQ ID NO: 2 as it is (or with mutation to amino acid residues) to transform a host cell, and harvesting the protein having the above activity from the culture. In addition, the enzyme can also be obtained by chemically synthesizing polypeptide that forms the enzyme.

A structure of the polynucleotide encoding the enzyme described above is not particularly limited. For example, the polynucleotide preferably has a base sequence having identity of 60% or greater, 65% or greater, 70% or greater, 75% or greater, 80% or greater, 85% or greater, 90% or greater, 91% or greater, 92% or greater, 93% or greater, 94% or greater, 95% or greater, 96% or greater, 97% or greater, 98% or greater, and 99% or greater with the base sequence of SEQ ID NO: 1.

The identity of the base sequences can be calculated using analytical tools (such as BLAST) that are commercially available or available through an electrical communication line (Internet). When using BLAST, various parameters can be calculated at initial conditions.

The polynucleotide may be any of the DNA, RNA, or DNA-RNA hybrids. The polynucleotide is preferably isolated. In a case where the polynucleotide is DNA, it may be cDNA.

Polynucleotides can be obtained by any method. For example, it can be produced and obtained using a chemical synthesis method (for example, a solid phase synthesis method using a phosphoramidite method) based on the information of SEQ ID NO: 1. It can also be readily prepared by using standard genetic engineering techniques, molecular biology techniques, biochemical techniques, and the like.

The vector preferably incorporates a polynucleotide encoding the enzyme. The type of vector is not particularly limited, and can be appropriately selected according to the type of host cell. Examples thereof include a plasmid vector, a cosmido vector, a phage vector, and a viral vector (an adenoviral vector, an adeno-associated viral vector, a retroviral vector, and a herpesvirus vector).

The vector is not limited to the configuration thereof as long as the polynucleotide can be expressed in the host. The vector preferably has other base sequences necessary for the expression of the polynucleotide. Examples of other base sequences include a promoter sequence, a leader sequence, a signal sequence, an enhancer sequence, and a ribosome binding sequence.

The transformant preferably contains a polynucleotide encoding the enzyme described above. Such a transformant can be obtained by introducing a vector containing the polynucleotide described above into the host. The host cell is not particularly limited as long as the host cell is capable of expressing the polynucleotide described above to produce the enzyme. Specific examples include a prokaryotic cell such as E. coli and B. subtilis, eukaryotic cells such as yeast, mold, insect cells, and mammalian cells. Transformation of the host using the vector can be performed according to a general method (for example, a calcium chloride method, an electroporation method, a microinjection method, and a lipofection method).

The enzyme described above can be obtained by culturing the above transformants. The culture conditions can be appropriately set according to the type of host or the like. After cultivation, the enzyme can be collected from a culture solution or a bacterial cell. In a case where an organism that secretes the enzyme out of the bacterial cell is used, the enzyme can be obtained by, for example, filtering, centrifuging, or the like to remove the insoluble matter, and then the enzyme can be obtained by performing isolation and purification by suitably combining concentration with ultra-filtration membrane, salting out dialyses such as ammonium sulfate precipitation, and various chromatographies. In this way, the enzyme described above can be mass-produced at low cost.

In one embodiment, the enzyme has excellent thermal stability. Therefore, it is useful and convenient to use the enzyme for a heat treatment in the isolation and purification. The host cells and culture supernatants obtained from the culture contain various proteins derived from the host cells. However, by performing the heat treatment, contaminant proteins derived from the host cells are denatured and condensed. In contrast, the enzyme having the excellent thermal stability does not cause denaturation, and therefore, can be easily separated from contaminant proteins derived from the host by centrifugation or the like. The conditions of the heat treatment are not particularly limited, and for example, it can be treated for 10 to 30 minutes at approximately 50° C. to 65° C. By subjecting the culture solution to the heat treatment as is or in a crude extract, other proteins can be inactivated and thereby a desired enzyme can be efficiently obtained.

The D-amino acid can be synthesized by utilizing the enzyme described above. The D-amino acid synthesis can be performed, for example, by the amination of 2-oxo acid, which is a substrate. In the presence of NADPH (or NADH) and ammonia, the enzyme can be reacted with 2-oxo acid as the substrate and the D-amino acid produced in a catalytic reaction of the enzyme can be collected. The D-amino acid collection can be performed in any method (for example, using an ion-exchange resin). Similarly, the enzyme described above can be used to produce the 2-oxo acid from the D-amino acid.

D-Alanine can be obtained by an action of the enzyme described above on 2-oxopropanoic acid. In one embodiment, in the production of D-alanine, it is preferable to use an enzyme without mutations of Asp95Ser, Met155Leu, Val159Gly, Thr174Ile, Arg184Met, and His230Asn in SEQ ID NO: 2 or an amino acid sequence having 80% or more identity thereof.

D-Valine can be obtained by an action of the enzyme described above on 2-oxo-3-methylbutanoic acid. In one embodiment, in the production of D-valine, it is preferable to use an enzyme having substitutions of Thr174Ile, Arg184Met, His230Asn, and His230Asn or substitutions of Thr174Ile, Arg184Met, His230Asn, Met155Leu, and Val159Gly in SEQ ID NO: 2 or an amino acid sequence having 80% or more identity thereof.

D-Leucine can be obtained by an action of the enzyme described above on 2-oxo-4-methylpentanoic acid. In one embodiment, in the production of D-leucine, it is preferable to use an enzyme having substitutions of Thr174Ile, Arg184Met, His230Asn, and His230Asn or substitutions of Thr174Ile, Arg184Met, His230Asn, Met155Leu, and Val159Gly in SEQ ID NO: 2 or an amino acid sequence having 80% or more identity thereof.

D-Isoleucine can be obtained by an action of the enzyme described above on 2-oxo-3-methylpentanoic acid. In one embodiment, in the production of D-isoleucine, it is preferable to use an enzyme having substitutions of Thr174Ile, Arg184Met, His230Asn, and His230Asn or substitutions of Thr174Ile, Arg184Met, His230Asn, Met155Leu, and Val159Gly in SEQ ID NO: 2 or an amino acid sequence having 80% or more identity thereof.

D-Methionine can be obtained by an action of the enzyme described above on 2-oxo-4-(methylthio) butanoic acid. In one embodiment, in the production of D-methionine, it is preferable to use an enzyme having substitutions of Thr174Ile, Arg184Met, His230Asn, and His230Asn or substitutions of Thr174Ile, Arg184Met, His230Asn, Met155Leu, and Val159Gly in SEQ ID NO: 2 or an amino acid sequence having 80% or greater identity thereof.

D-Phenylalanine can be obtained by an action of the enzyme described above on 2-oxo-3-phenylpropanoic acid. In one embodiment, in the production of D-phenylalanine, it is preferable to use an enzyme with substitutions of Thr174Ile, Arg184Met, His230Asn, Met155Leu, and Val159Gly (or additional substitution of Asp95Ser), in SEQ ID NO: 2 or an amino acid sequence having 80% or more identity thereof.

D-Aspartic acid can be obtained by an action of the enzyme described above on 2-oxobutanedioic acid. In one embodiment, in the production of D-aspartic acid, it is preferable to use an enzyme without substitutions of Thr174Ile, Arg184Met, His230Asn, Asp95Ser, Met155Leu, and Val159Gly in SEQ ID NO: 2 or an amino acid sequence having 80% or more identity thereof.

D-Glutamic acid can be obtained by an action of the enzyme described above on 2-oxoglutaric acid. In one embodiment, in the production of D-glutamic acid, it is preferable to use an enzyme without substitutions of Thr174Ile, Arg184Met, His230Asn, Asp95Ser, Met155Leu, and Val159Gly in SEQ ID NO: 2 or an amino acid sequence having 80% or more identity thereof.

D-2-Aminobutyric acid can be obtained by an action of the enzyme described above on 2-oxobutanoic acid. In one embodiment, in the production of D-2-aminobutyric acid, it is preferable to use an enzyme with substitutions of Thr174Ile, Arg184Met, and His230Asn in SEQ ID NO: 2 or an amino acid sequence having 80% or greater identity thereof.

D-2-Aminooctanoic acid can be obtained by an action of the enzyme described above on 2-oxobutanoic acid. In one embodiment, in the production of D-2-aminooctanoic acid, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-2-Aminoheptanoic acid can be obtained by an action of the enzyme described above on 2-oxoheptanoic acid. In one embodiment, in the production of D-2-aminoheptanoic acid, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or greater identity thereof.

D-Norleucine can be obtained by an action of the enzyme described above on 2-oxohexanoic acid. In one embodiment, in the production of D-norleucine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Norvaline can be obtained by an action of the enzyme described above on 2-oxopentanoic acid. In one embodiment, in the production of D-norvaline, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Serine can be obtained by an action of the enzyme described above on 2-oxo-3-hydroxypropionic acid. In one embodiment, in the production of D-serine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Threonine can be obtained by an action of the enzyme described above on 2-3-hydroxybutanoic acid. In one embodiment, in the production of D-threonine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Cysteine can be obtained by an action of the enzyme described above on 2-oxo-3-sulfanylpropanoic acid. In one embodiment, in the production of D-cysteine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or greater identity thereof.

D-Asparagine can be obtained by an action of the enzyme described above on 2-oxo-3-carbamoylpropanoic acid. In one embodiment, in the production of D-asparagine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Glutamine can be obtained by an action of the enzyme described above on 2-oxo-4-carbamoylbutanoic acid. In one embodiment, in the production of D-glutamine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Tryptophan can be obtained by an action of the enzyme described above on 2-oxo-3-(1H-indol-3-yl) propanoic acid. In one embodiment, in the production of D-tryptophan, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Lysine can be obtained by an action of the enzyme described above on 2-oxo-6-amino caproic acid. In one embodiment, in the production of D-lysine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Arginine can be obtained by an action of the enzyme described above on 2-oxo-5-guanidinopentanoic acid. In one embodiment, in the production of D-arginine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

D-Tyrosine can be obtained by an action of the enzyme described above on 2-oxo-3-(4-hydroxyphenyl) propanoic acid. In one embodiment, in the production of D-tyrosine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or greater identity thereof.

D-Histidine can be obtained by an action of the enzyme described above on 2-oxo-3-(4-imidazolyl) propionic acid. In one embodiment, in the production of D-histidine, it is preferable to use an enzyme having substitutions of Thr174Ile, Arg184Met, and His230Asn or substitutions of Thr174Ile, Arg184Met, His230Asn, Met155Leu, and Val159Gly (or additional substitution of Asp95Ser) in SEQ ID NO: 2 or an amino acid sequence having 80% or more identity thereof.

EXAMPLES

Hereinafter, the present invention will be described in detail using examples and comparative examples; however, the present invention is not limited to these examples.

Example 1 Cloning of D-Type Amino Acid Dehydrogenase Gene and Production of Expression Vector The D-type amino acid dehydrogenase gene can be obtained using known gene cloning techniques. For example, a gene can be synthesized and acquired based on sequence information that can be obtained by searching a publicly known database such as GenBank.

DNA encoding a D-type amino acid dehydrogenase having a base sequence of SEQ ID NO: 1, derived from *N. massiliense* was acquired from GENEWIZ. This was cleaved with restriction enzymes NdeI and EcoRI, separated by agarose gel electrophoresis, and then extracted and purified from the gel. DNA fragments after a restriction enzyme treatment were incorporated into restriction enzyme sites (NdeI and EcoRI) of pET-21a(+) (available from Novagen) of a plasmid for protein expression by a ligation reaction to construct an expression vector that retains the D-type amino acid dehydrogenase gene. The expression vector was constructed such that the D-type amino acid dehydrogenase gene derived from *N. masiliense* is incorporated into downstream of a T7 promoter and a liposome binding site, and upstream of a T7 terminator. The base sequence (SEQ ID NO: 1) of this D-type amino acid dehydrogenase gene is illustrated in FIG. 1. In addition, the amino acid sequence (SEQ ID NO: 2) encoded by the base sequence of SEQ ID NO: 1 is also illustrated in FIG. 2.

Note that the expression vector does not include a histidine-tag. In addition, when inserting the D-type amino acid dehydrogenase gene into another expression vector, a stop codon (utilizing TAA in this example) can also be added to the D-type amino acid dehydrogenase gene to design the base sequence to prevent translation of the histidine-tag following the base sequence.

Example 2 Synthesis of D-Type Amino Acid Dehydrogenase

An *E. coli* BL21 (DE3) strain was transformed using an expression vector obtained in Example 1 described above. This was inoculated into a LB medium (500 mL) containing antibiotic ampicillin (final concentration of 100 mg/L) and shaken at 37° C. until approximately $A_{600}$=0.6, and then isopropyl-beta-D(−)-galactopyranoside (available from Wako Pure Chemical Industries, Ltd.) was added to be at a final concentration of 0.1 mM, and shaken for another 6 hours at 37° C.

The strains in a culture solution were collected by centrifugation and these strains were suspended using 50 mM of a phosphate buffer solution (pH 7.2) and sonicated under ice-cooling conditions. After sonication, the obtained supernatant was set as a crude enzyme solution. The crude enzyme solution was heat-treated at 50° C. for 30 minutes, and the treated enzyme solution was subjected to TOYOPEARL SuperQ-650 anion exchange chromatography (available from Tosoh Corporation); TOYOPEARL Butyl-650 M hydrophobic chromatography (available from Tosoh Corporation), and Superdex200 gel filtration chromatography (available from GE Healthcare Japan Corporation) for purification. The concentration of the obtained D-type amino acid dehydrogenase was measured by a Bradford method.

FIG. 3 illustrates a result of SDS-PAGE of a crude enzyme solution, a heat-treated enzyme solution, and active fractions obtained after various chromatographies and a molecular weight marker. From lane 6 of FIG. 1, it was possible to confirm a single band of protein at 32 kDa, and thus to obtain the excellent purification results.

Example 3 Confirmation of Coenzyme Dependence of D-Type Amino Acid Dehydrogenase The coenzyme dependence was evaluated for the D-type amino acid dehydrogenase obtained in Example 2 above. The coenzyme dependence of the enzyme was evaluated by an activity-staining method due to a catalytic reaction of the enzyme.

More specifically, an appropriate amount of enzyme solution was subjected to disc gel electrophoresis. The gel after electrophoresis was immersed in a reaction solution containing 200 mM of phosphate buffer solution (pH 8.0), 10 mM of meso-diaminopimelic acid, 0.1 mM of 2-(4-iodophenyl)-3-(4-nitrophenyl)-5-phenyl-2H-tetrazolium chloride (INT) (available from Dojindo Molecular Technologies, Inc.), 0.04 mM of 1-methoxy-5-methylphenazinium methyl sulfate (PMS) (available from Dojindo Molecular Technologies, Inc.), and 1.25 mM of various coenzymes, and kept at 50° C. for 30 minutes. The 2-(4-iodophenyl)-3-(4-nitrophenyl)-5-phenyl-2H-tetrazolium chloride in the reaction solution is reduced to form a water-soluble formazan. A reaction formula is indicated below. In the following reaction formula, the D-type amino acid dehydrogenase is referred to as "meso-DAPDH".

[Chemical Formula 1]

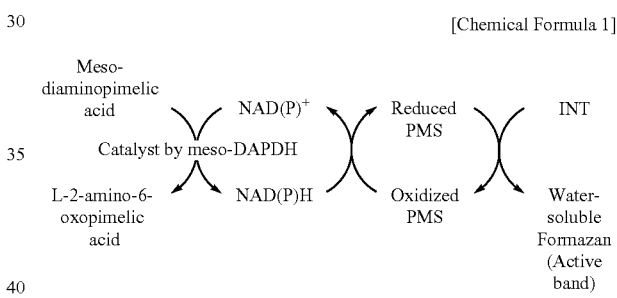

FIG. 4 illustrates the results of protein staining and activity-staining of a purified enzyme. A single band due to the enzyme was confirmed from each lane in FIG. 4. It was also confirmed from lanes 2 and 3 that the enzyme utilized both $NAD^+$ and $NADP^+$ coenzymes.

Example 4 Confirmation of Optimum PH in Catalytic Reaction of D-Type Amino Acid Dehydrogenase The optimum pH was evaluated for the D-type amino acid dehydrogenase obtained in Example 2. The activity of the enzyme was measured by determining an increase in absorbance at wavelength of 340 nm of NADPH produced by the catalytic reaction of the enzyme.

More specifically, the reaction solution was prepared by mixing an appropriate amount of enzyme solution in 200 mM various buffer solutions containing 10 mM meso-diaminopimelic acid and 1.25 mM $NADP^+$. Next, the activity was determined by measuring the increase in absorbance at 340 nm with changes from $NADP^+$ to NADPH in this reaction solution at a reaction temperature of 50° C.

The absorbance was measured by an ultraviolet-visible spectrophotometer UV-1800 (available from SHIMADZU). The specific activity of the enzyme was calculated from the concentration of the enzyme used and enzyme dilution rate using the obtained absorbance change and the following equation.

$$\text{Specific activity} = \frac{\Delta A340 \cdot D}{6.22 \cdot C \cdot d} \quad \text{(Equation 1)}$$

ΔA340: Amount of absorbance change per minute at 340 nm
D: Enzyme dilution rate
6.22: Millimolar molecular absorptivity (L·mmol$^{-1}$·cm$^{-1}$) of NADPH at 340 nm
C: Protein concentration (mg/mL)
d: Optical path length (1 cm)

The measurement results are illustrated in FIG. 5. The results indicate that the optimum pH for activity in the deamination of meso-diaminopimelic acid is 10.5.

Example 5 Confirmation of Optimum Temperature in Catalytic Reaction of D-Type Amino Acid Dehydrogenase The absorbance was measured in the same manner as in Example 4 except that 1.25 mM of NADP$^+$ was added to the reaction solution heated at a predetermined temperature (50° C., 55° C., 60° C., 65° C., 70° C., 75° C., or 80° C.) and the increase in absorbance was immediately measured to determine the relative activity. The measurement results are illustrated in FIG. 6. From the results, it was confirmed that the optimum temperature for activity was about 75° C.

Example 6 Confirmation of Thermal Stability of D-Type Amino Acid Dehydrogenase

The D-type amino acid dehydrogenase purified in Example 2 was heat-treated in 10 mM phosphate buffer solution (pH 7.2) under various temperature conditions (40° C., 45° C., 50° C., 55° C., 60° C., 65° C., or 70° C.) for 30 minutes to confirm residual activity after being left to stand for 5 minutes on ice. Enzymatic activity was evaluated by the increase in the absorbance at 340 nm due to the formation of NADPH in a case of using meso-diaminopimelic acid as a substrate in the method described in Example 4. The residual activity after treatment at other temperatures was calculated as a relative activity with treatment at 40° C. as 100%.

Figure 7:
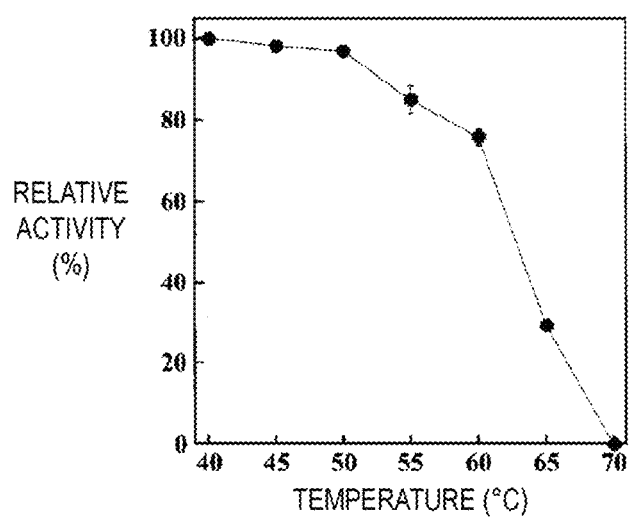
FIG. 7 illustrates a result of measurement of thermostability of the enzyme. A horizontal axis indicates a heat treatment temperature (° C.) and a vertical axis indicates a relative activity (%).

The measurement results are illustrated in FIG. 7. From the results, it was confirmed that the enzyme retained about 76% residual activity after the heat treatment at 60° C.

Example 7 Confirmation of PH Stability of D-Type Amino Acid Dehydrogenase

The D-type amino acid dehydrogenase purified in Example 2 was subjected to a heat treatment at 50° C., in 100 mM of each buffer solution (pH 4.0, 4.5, 5.0, 5.5, 6.0, 6.5, 7.0, 7.5, 8.0, 8.5, 9.0, 9.5, 10.0, 10.5, 11.0, 11.3, 12.0, 12.3, or 13.0) for 30 minutes to confirm residual activity after being left to stand for 5 minutes on ice. Enzymatic activity was evaluated by the increase in the absorbance at 340 nm due to the formation of NADPH in a case of using meso-diaminopimelic acid as a substrate in the method described in Example 4. The residual activity after treatment at other pH was calculated as a relative activity with treatment at pH 5.5 as 100%.

Figure 8:
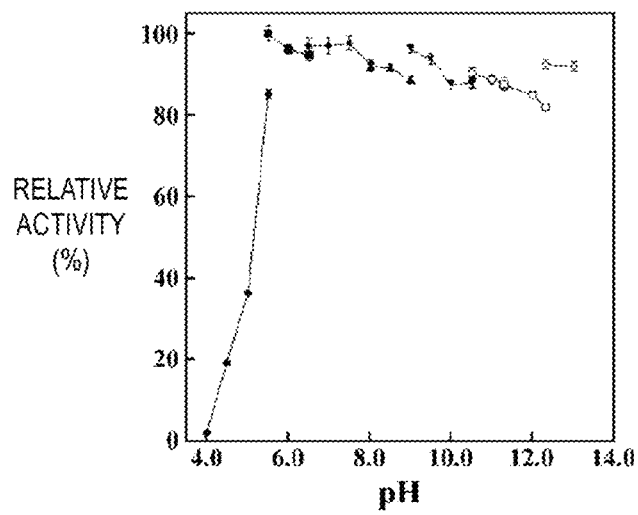
FIG. 8 illustrates a result of measurement of pH stability of the enzyme. A horizontal axis indicates temperature for measurement (pH) and a vertical axis indicates a relative activity (%). ● indicates an acetate buffer solution, ■ indicates a citrate buffer solution, ♦ indicates a phosphate buffer solution, ▲ indicates a borate buffer solution, ▼ indicates a glycine buffer solution, ○ indicates a carbonate buffer solution, □ indicates a phosphate buffer solution, and ◊ indicates a potassium chloride buffer solution.

The measurement results are illustrated in FIG. 8. As illustrated in FIG. 8, the D-type amino acid dehydrogenase retained a residual activity of about 90% or more after treatment with pH 5.5 to 9.5.

Example 8 Kinetic Analysis of D-Type Amino Acid Dehydrogenase

For the D-type amino acid dehydrogenase obtained in Example 2, a kinetic analysis was performed by using meso-diaminopimelic acid as a substrate, and NADP$^+$ or NAD$^+$ as the coenzyme.

A turnover number ($k_{cat}$) as a reaction rate parameter, a Michaelis constant ($K_m$) value, and catalytic efficiency ($k_{cat}/K_m$) were determined with Igor Pro ver. 3.14 (available from WaveMetrics) based on Michaelis-Menten equation after the initial velocities were plotted against different substrates and coenzyme concentrations. Enzymatic activity was evaluated by the increase in the absorbance at 340 nm due to the formation of NAD(P)H in a case of using meso-diaminopimelic acid as a substrate in the method described in Example 4.

Table 2 indicates the kinetic analysis results for the purified enzyme. As indicated in Table 2, in the D-type amino acid dehydrogenase, the use of NADP$^+$ for the coenzyme rather than NAD$^+$ resulted in higher catalytic efficiencies.

TABLE 2

| Kinetic analysis | | | |
|---|---|---|---|
| Substrate Coenzyme | $k_{cat}$ (min$^{-1}$) | $K_m$ (mM) | $k_{cat}/K_m$ (min$^{-1}$*mM$^{-1}$) |
| Meso-diaminopimelic acid | 3.83 × 10$^1$ | 3.34 | 1.15 × 10$^4$ |
| NAD$^1$ | 5.36 × 10$^5$ | 890 | 6.02 × 10$^2$ |
| NAPD$^1$ | 4.75 × 10$^4$ | 0.302 | 1.57 × 10$^5$ |

The $k_{cat}$, $K_m$, and $k_{cat}/K_m$ for meso-diaminopimelic acid were determined using NADP$^+$ as the coenzyme.

Example 9 Crystallization of D-Type Amino Acid Dehydrogenase

Figure 9:
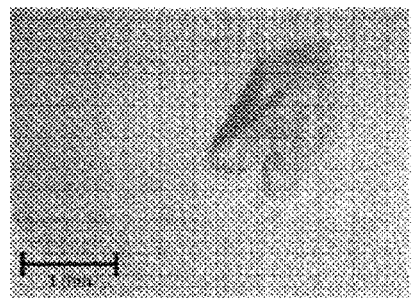
FIG. 9 illustrates meso-DAPDH crystals derived from *N. massiliense*.

The purified D-type amino acid dehydrogenase (concentration of 17.80 mg/mL) solution and a crystallization solution consisting of 1.0 M of 1,6-hexanediol, 0.1 M of sodium acetate trihydrate (pH 4.6), and 0.01 M of cobalt chloride (II) hexahydrate were mixed in the same amount (0.5 μL each). On a 96-well plate (Hampton Research Co., Ltd.), 50 μL of the crystallization solution which was used as a mother liquor was left to stand at 20° C. by a vapor diffusion using a sitting drop method. Crystals precipitated after 1 day and grew to crystals of measurable size (approximately 1.5×1.0× 1.0 mm) after 3 days (FIG. 9).

Example 10 Crystal Structural Analysis of D-Type Amino Acid Dehydrogenase

Since the crystal deteriorated due to X-ray damage and a resolution gradually decreased in a room temperature measurement, the crystal of the D-type amino acid dehydrogenase was measured under the low temperature condition.

After the crystal was transferred to a crystallization solution containing 30% glycerol, 90K nitrogen gas was purged into the crystallized solution and rapidly cooled. X-ray diffraction data of 1.42 Å resolution was collected using an X-ray diffraction apparatus of MX300HE detector (available from Raynonix) to determine a crystallographic parameter. A space group was $P2_12_12_1$ and the lattice constant was a=128.83 Å, b=129.80 Å, c=136.34 Å, $\alpha$=90°, $\beta$=90°, $\gamma$=90°. Assuming that six molecules were included in an asymmetric unit, a moisture content of the crystals was 57.7%.

Example 11 Solid Structure Determination of D-Type Amino Acid Dehydrogenase

The X-ray diffraction intensity data obtained in Example 10 was used to carry out a molecular replacement method using a program PHASER for determining the three dimensional structure of D-type amino acid dehydrogenase. The three-dimensional structural coordinates of meso-DAPDH derived from *Symbiobacterium thermophilum* were used as a search model for calculation of molecular replacement. Calculations using structural factors from 50.0 Å to 1.42 Å resolution resulted in one significant solution.

The obtained structural model was refined using X-ray diffraction data from 30.0 Å to 1.42 Å resolution by the method of restraint refinement in program REFMAC5. As a result, amino acid residues Val4-Val302 were assigned in both A and B molecules of meso-DAPDH. Additionally, 2609 water molecules were assigned by the electron density map. At a final stage of refinement, an R factor was 13.7% and Free-R factor was 18.3%. Furthermore, a root-mean-square deviation from an ideal state of bond distances and bond angles between atomic positions was 0.03 Å and 2.66 degrees, respectively.

Figures 10, 11:
FIG. 10 illustrates a three-dimensional structure of meso-DAPDH derived from *N. massiliense*.
FIG. 11 illustrates an alignment of the amino acid sequence of the D-type amino acid dehydrogenase derived from *N. massiliense* (SEQ ID NO: 2) and D-type amino acid sequences of other four types of meso-diaminopimelic acid dehydrogenases. The above other four types of meso-diaminopimelic acid dehydrogenases are those derived from *Bacillus sphaericus* (SEQ ID NO: 3), *Corynebacterium glutamicum* (SEQ ID NO: 4); *Symbiobacterium thermophilum* (SEQ ID NO: 5), and *Ureibacillus thermosphaericus* (SEQ ID NO: 6).

The three-dimensional structural coordinates were obtained by the analysis above. It was confirmed from the obtained structural coordinates that the oligomeric state of the D-type amino acid dehydrogenase is a hexamer (FIG. 10).

Example 12 Synthesis of Modified D-Type Amino Acid Dehydrogenase

DNA encoding polypeptide in which three types of mutations (Thr174Ile, Arg184Met, and His230Asn) were introduced into the amino acid sequence of D-type amino acid dehydrogenase derived from *N. massiliense* was obtained by synthesis. This was cleaved with restriction enzymes NdeI and EcoRI, separated by agarose gel electrophoresis, and then extracted and purified from the gel. DNA fragments after a restriction enzyme treatment were incorporated into restriction enzyme sites (NdeI and EcoRI) of pET-21a(+) (available from Novagen) of a plasmid for protein expression by a ligation reaction to construct an expression vector that retains three-mutation introduced D-type amino acid dehydrogenase gene. The expression vector was constructed such that the three-mutation introduced D-type amino acid dehydrogenase gene was incorporated into downstream of the T7 promoter and the liposome binding site, and upstream of the T7 terminator. The base sequence (SEQ ID NO: 7) of the three-mutation introduced D-type amino acid dehydrogenase gene is illustrated in FIG. 12. In addition, the amino acid sequence (SEQ ID NO: 8) encoded by the base sequence of SEQ ID NO: 7 is also illustrated in FIG. 13.

The expression vector described above does not include a histidine-tag. In addition, when inserting the D-type amino acid dehydrogenase gene into another expression vector, a stop codon (utilizing TAA in this example) can also be added to the D-type amino acid dehydrogenase gene to design the base sequence to prevent translation of the histidine-tag following the base sequence.

DNA encoding polypeptide into which six types of mutations (Asp95Ser, Met155Leu, Val159Gly, Thr174Ile, Arg184Met, and His230Asn) were introduced into the amino acid sequence of D-type amino acid dehydrogenase derived from *N. massiliense* was obtained by synthesis. An expression vector that retains the six-mutation introduced D-type amino acid dehydrogenase gene was further constructed in the same manner as described above. The base sequence (SEQ ID NO: 9) of the six-mutation introduced D-type amino acid dehydrogenase gene is illustrated in FIG. 14. In addition, the amino acid sequence (SEQ ID NO: 10) encoded by the base sequence of SEQ ID NO: 9 is also illustrated in FIG. 15.

In order to prepare a gene for a mutant enzyme in which five types of mutations (Met155Leu, Val159Gly, Thr174Ile, Arg184Met, and His230Asn) are introduced into the D-type amino acid dehydrogenase derived from *N. massiliense*, the six mutation-introduced D-type amino acid dehydrogenase/pET-21a(+) prepared above was used as a template to prepare the expression vector by PCR using "PrimeSTAR Max DNA Polymerase" available from Takara Bio Inc. PCR was performed according to the manufacturer's protocol. A PCR reaction solution was prepared by containing 0.3 μM of each of the following primers and 50 ng of templet DNA as described above.

```
                                          (SEQ ID NO: 11)
5'-CGGTCGACAGTTACGACATTCACGGCGAAC-3'

(SEQ ID NO: 12)
5'-GTTCGCCGTGAATGTCGTAACTGTCGACCG-3'
```

After PCR, 2 μL of DpnI was added to the reaction solution and treated at 37° C. for 1 hour, and *E. coli* DH5α was transformed by using the solution after treatment. Transformed cells were applied onto a LB agar medium plate containing antibiotic ampicillin (final concentration of 100 mg/L) and cultured at 37° C. for 16 hours. The generated colonies were harvested and cultured in LB liquid medium containing ampicillin overnight. After collection of the strains from the culture solution by centrifugation, five mutation-introduced D-type amino acid dehydrogenase/pET-21a(+) was collected according to the manufacturer's protocol using AccuPrep Plasmid Mini Extraction Kit (BIONEER). The base sequence (SEQ ID NO: 13) of the five-mutation introduced D-type amino acid dehydrogenase gene is illustrated in FIG. 16. In addition, the amino acid sequence (SEQ ID NO: 14) encoded by the base sequence of SEQ ID NO: 13 is also illustrated in FIG. 17.

An *E. coli* BL21 (DE3) strain was transformed using the various expression vectors or D-type amino acid dehydrogenase/pET-21a(+) obtained above. These were inoculated into 250 mL of Overnight Express Instant LB medium containing ampicillin (available from Merck Millipore) and cultured for 16 hours at 37° C.

Each of the strains in the culture solution was collected by centrifugation and each strain was suspended using 50 mM of a phosphate buffer solution (pH 7.2) and sonicated under ice-cold conditions. After sonication, the obtained supernatant was used as a crude enzyme solution. The crude enzyme solution was heat-treated at 50° C. for 30 minutes, and the treated enzyme solution was subjected to TOYOPEARL SuperQ-650 anion exchange chromatography (available from Tosoh Corporation); TOYOPEARL Butyl-650 M hydrophobic chromatography (available from Tosoh Corporation), and Superdex200 gel filtration chromatography (available from GE Healthcare Japan Corporation) for purification. The concentration of the purified enzymes was measured by a Bradford method.

Example 13 Confirmation of Activity of D-Type Amino Acid Dehydrogenase

The activity was evaluated for the D-type amino acid dehydrogenase obtained in Example 2 above. The activity of the enzyme was evaluated by an activity-staining method due to a catalytic reaction of the enzyme. More specifically, an appropriate amount of enzyme solution was subjected to disc gel electrophoresis. The gel after electrophoresis was immersed in a reaction solution containing 200 mM of phosphate buffer solution (pH 8.0), 10 mM of D-alanine or L-alanine, 0.1 mM of 2-(4-iodophenyl)-3-(4-nitrophenyl)-5-phenyl-2H-tetrazolium chloride (INT) (available from Dojindo Molecular Technologies, Inc.), 0.04 mM of 1-methoxy-5-methylphenazinium methyl sulfate (PMS) (available from Dojindo Molecular Technologies, Inc.), and 1.25 mM of NADP$^+$, and kept at 50° C. for 30 minutes. 2-(4-iodophenyl)-3-(4-nitrophenyl)-5-phenyl-2H-tetrazolium chloride in the reaction solution is reduced to form a water-soluble formazan. A reaction formula is indicated below. In the following reaction formula, the D-type amino acid dehydrogenase is referred to as "meso-DAPDH".

[Chemical Formula 2]

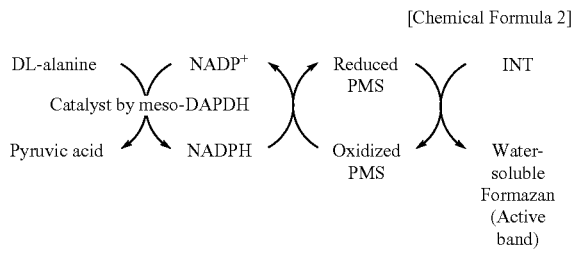

FIG. 18 illustrates the results of protein staining and activity-staining of the purified D-type amino acid dehydrogenase. A single band due to the enzyme was confirmed from lanes 1 and 2 in FIG. 18. From lane 2, it was also confirmed that the enzyme selectively acts on the D-amino acid. Also, the D-type amino acid dehydrogenase reversibly catalyzes the deamination of the D-amino acid. Therefore, it was confirmed that the D-type amino acid dehydrogenase synthesized the D-amino acid rather than the L-amino acid by the amination of 2-oxo acid.

Example 14 Confirmation of D-Amino Acid Synthesis Activity of Each Enzyme

The D-amino acid synthesis activity of the D-type amino acid dehydrogenase the various enzymes and its mutants obtained in Examples 2 and 12 was measured, and the effect of various mutation was investigated. The activity of the enzyme was measured by determining a decrease in absorbance at wavelength of 340 nm of NADPH or NADH produced by the catalytic reaction of the enzyme. More specifically, the reaction solution was prepared by mixing an appropriate amount of enzyme solution in 200 mM of glycine-KOH buffer solution (pH 9.5) containing 5 mM of 2-oxo acid, 0.1 mM of NAD(P)H, 200 mM of ammonium chloride. Next, the enzymatic activity was determined by measuring the decrease in absorbance at 340 nm with changes from NAD(P)H to NAD(P)$^+$ in this reaction solution at a reaction temperature of 50° C. The absorbance was measured by an ultraviolet-visible spectrophotometer UV-1800 (available from SHIMADZU). The enzymatic activity was assayed by measuring absorbance change and the same equation as used in Example 4, and the specific activity of the enzyme was calculated from the concentration of the enzyme used and enzyme dilution rate. Table 3 illustrates the D-amino acid synthesis activity for each enzyme.

TABLE 3

| | Wild type | | Three-mutation enzyme | | Five-minute enzyme | | Six-mutation enzyme | |
|---|---|---|---|---|---|---|---|---|
| 2-Oxo-acid/ synthesized D-amino acid | NADPH μmol/min/ mg | NADH μmol/min/ mg | NADPH μmol/min/ mg | NADH μmol/min/ mg | NADPH μmol/min/ mg | NADH μmol/min/ mg | NADPH μmol/min/ mg | NADH μmol/min/ mg |
| 2-oxopropanoic acid/D-alanine | 4.7 ± 0.070 | 0.13 ± 0.0025 | 2.2 ± 0.010 | 0.000 ± 0.0028 | 0.30 ± 0.017 | 0.046 ± 0.00089 | 0.0070 ± 0.010 | 0.12 ± 0.0031 |
| 2-oxo-3-methylbutanoic acid/D-valine | 0.26 ± 0.0050 | 0.0012 ± 0.00047 | 2.5 ± 0.043 | 0.043 ± 0.0049 | 2.4 ± 0.030 | 0.018 ± 0.00028 | 0.051 ± 0.0017 | No Activity |
| 2-oxo-4-methylpentanoic acid/D-leucine | 0.803 ± 0.016 | No Activity | 4.6 ± 0.055 | 0.044 ± 0.0046 | 9.0 ± 0.064 | 0.055 ± 0.0016 | 1.2 ± 0.021 | 0.011 ± 0.00070 |
| 2-oxo-3-methylpentanoic acid/D-isoleucine | 0.18 ± 0.016 | No Activity | 4.7 ± 0.13 | 0.043 ± 0.0061 | 4.0 ± 0.083 | 0.025 ± 0.00049 | 0.23 ± 0.0030 | 0.0030 ± 0.0012 |
| 2-oxo-4-(methylthio) butanoic acid/D-methionine | 2.0 ± 0.028 | No Activity | 5.2 ± 0.040 | 0.013 ± 0.0018 | 12.3 ± 0.49 | 0.069 ± 0.0023 | 2.8 ± 0.027 | 0.024 ± 0.00070 |
| 2-oxo-3-phenylpropanoic acid/D-phenylalanine | 1.5 ± 0.077 | 0.011 ± 0.0044 | 1.5 ± 0.023 | 0.028 ± 0.0035 | 2.7 ± 0.026 | 0.012 ± 0.0014 | 2.1 ± 0.020 | 0.018 ± 0.0026 |
| 2-oxobutanedioic acid/D-aspartic acid | 5.2 ± 0.083 | 0.13 ± 0.0014 | 2.0 ± 0.18 | 0.12 ± 0.095 | 0.39 ± 0.074 | 0.25 ± 0.21 | 0.44 ± 0.019 | 0.14 ± 0.0061 |
| 2-oxoglutaric acid/ | 0.11 ± | No | No | No | No | No | No | No |

TABLE 3-continued

| | Wild type | | Three-mutation enzyme | | Five-minute enzyme | | Six-mutation enzyme | |
|---|---|---|---|---|---|---|---|---|
| 2-Oxo-acid/ synthesized D-amino acid | NADPH µmol/min/ mg | NADH µmol/min/ mg | NADPH µmol/min/ mg | NADH µmol/min/ mg | NADPH µmol/min/ mg | NADH µmol/min/ mg | NADPH µmol/min/ mg | NADH µmol/min/ mg |
| D-glutamic acid | 0.0042 | Activity | Activity | Activity | Activity | Activity | Activity | Activity |
| 2-oxobutanoic acid/ D-2-aminobutyric acid | 1.4 ± 0.0050 | 0.011 ± 0.00036 | 2.2 ± 0.051 | 0.028 ± 0.0070 | 1.6 ± 0.027 | 0.014 ± 0.0013 | 0.027 ± 0.0046 | 0.0011 ± 0.00044 |
| 2-oxooctanoic acid/ D-2-aminooctanoic acid | 5.8 ± 0.11 | No Activity | 8.2 ± 0.15 | 0.039 ± 0.0049 | 11.2 ± 0.14 | 0.050 ± 0.0017 | 9.0 ± 0.31 | 1.0 ± 0.039 |

From the results in Table 1, the D-type amino acid dehydrogenase without mutation synthesized various types of D-amino acids such as branched-chain D-amino acid, sulfur-containing D-amino acid, acidic D-amino acid, and aromatic D-amino acid, by using various 2-oxo acids as substrates. In addition, due to mutations into the D-type amino acid dehydrogenase, the activity of synthesizing the branched-chain D-amino acid and the sulfur-containing D-amino acid was increased to about 30 times. In addition, each mutant showed the NADH-dependent synthesis activity of D-amino acid, which was not detected in the enzyme without mutation.

SEQUENCE LISTING

P18-162WO_PCT_D-type amino acid dehydrogenase_20180807_113952_6.txt

The invention claimed is:

1. An enzyme comprising the following characteristics of (a) and (b):
   (a) the enzyme has reversible D-amino acid dehydrogenase activity; and
   (b) the enzyme is a hexamer of polypeptides, wherein each of the polypeptides of the hexamer comprises an amino acid sequence having at least 90% sequence identity with the amino acid sequence of SEQ ID NO: 2, and wherein one or more amino acids at the positions corresponding to Asp95, Met155, Val159, Thr174, Arg184, and His230 of SEQ ID NO: 2 is substituted with a different amino acid in the amino acid sequence of each of the polypeptides.

2. The enzyme according to claim 1, wherein the enzyme has an activity of producing D-aspartic acid from 2-oxobutanedioic acid.

3. The enzyme according to claim 1, wherein the enzyme is capable of utilizing both NADH and NADPH as coenzymes.

4. The enzyme according to claim 1, wherein the enzyme has a $k_{cat}$ of $1.0 \times 10^4$ min$^{-1}$ or greater in a case of using meso-diaminopimelic acid as the substrate.

5. The enzyme according to claim 1, wherein the enzyme has an optimum pH for activity of 10.5 in the case of using meso-diaminopimelic acid as the substrate.

6. The enzyme according to claim 1, wherein the enzyme has an optimum temperature for activity of 75 degrees in a case of using meso-diaminopimelic acid as the substrate.

7. The enzyme according to claim 1, wherein the one or more amino acid substitutions is selected from the group consisting of Asp95Ser, Met155Leu, Val159Gly, Thr174Ile, Arg184Met, and His230Asn, wherein the amino acid positions correspond to SEQ ID NO: 2.

8. A polynucleotide comprising a nucleotide sequence encoding the enzyme according to claim 1.

9. A vector comprising the polynucleotide according to claim 8.

10. An isolated transformant comprising the vector according to claim 9.

11. A method for producing an enzyme comprising:
    culturing the isolated transformant according to claim 10 under conditions suitable for production of the enzyme.

12. A method for producing a D-amino acid comprising contacting the enzyme according to claim 1 with a 2-oxo acid to thereby produce a D-amino acid.

* * * * *